(12) United States Patent
Huang et al.

(10) Patent No.: US 8,586,110 B2
(45) Date of Patent: Nov. 19, 2013

(54) **THERAPEUTIC COMPOSITION PRODUCED USING *CAMELLIA SINENSIS* LEAVES AND HYDROGEN PEROXIDE**

(71) Applicant: LiveLeaf, Inc., San Carlos, CA (US)

(72) Inventors: Alexander L Huang, Menlo Park, CA (US); Gin Wu, San Rafael, CA (US)

(73) Assignee: LiveLeaf, Inc., San Carlos, CA (US)

( * ) Notice: Subject to any disclaimer, the term of this patent is extended or adjusted under 35 U.S.C. 154(b) by 0 days.

(21) Appl. No.: 13/680,007

(22) Filed: Nov. 16, 2012

(65) Prior Publication Data

US 2013/0078322 A1  Mar. 28, 2013

Related U.S. Application Data

(63) Continuation of application No. 12/715,270, filed on Mar. 1, 2010, now Pat. No. 8,343,552, which is a continuation-in-part of application No. 12/317,638, filed on Dec. 23, 2008.

(60) Provisional application No. 61/209,260, filed on Mar. 4, 2009, provisional application No. 61/009,484, filed on Dec. 28, 2007.

(51) Int. Cl.
*A61K 36/00* (2006.01)
*A61K 36/82* (2006.01)

(52) U.S. Cl.
USPC .............................. 424/729; 424/725; 424/616

(58) Field of Classification Search
USPC .......................................... 424/729, 725, 616
See application file for complete search history.

(56) References Cited

U.S. PATENT DOCUMENTS

| | | | |
|---|---|---|---|
| 1,844,018 A | 2/1932 | Sailer | |
| 1,891,149 A | 12/1932 | Elger | |
| 1,965,458 A | 7/1934 | Elger | |
| 3,484,248 A * | 12/1969 | Graham et al. | 426/597 |
| 3,649,297 A * | 3/1972 | Millin | 426/49 |
| 3,692,904 A | 9/1972 | Tsutsumi | |
| 3,817,835 A | 6/1974 | Neidleman | |
| 3,821,440 A * | 6/1974 | Revee | 426/312 |
| 3,824,184 A | 7/1974 | Hatcher et al. | |
| 3,860,694 A | 1/1975 | Jayawant | |
| 3,864,454 A | 2/1975 | Pistor et al. | |
| 4,008,339 A | 2/1977 | Matsuda et al. | |

(Continued)

FOREIGN PATENT DOCUMENTS

| EP | 0390107 | 10/1990 |
|---|---|---|
| EP | 0797451 | 9/2004 |

(Continued)

OTHER PUBLICATIONS

U.S. Appl. No. 12/317,638, filed Dec. 23, 2008, Huang, et al.

(Continued)

*Primary Examiner* — Patricia Leith
(74) *Attorney, Agent, or Firm* — Brian S. Boyer; Syndicated Law PC

(57) ABSTRACT

Methods of and compositions for producing and using plant-based materials are provided. The methods include using biopolymers or their synthetic equivalents combined with a stable source of reactive oxygen species that when applied to or combined with a separate source of oxido-reducing enzyme or catalyst will cause the formation of an activated biopolymer with increased protein binding affinity and microbial control activities.

10 Claims, 5 Drawing Sheets

(56) References Cited

U.S. PATENT DOCUMENTS

| | | | |
|---|---|---|---|
| 4,072,671 | A | 2/1978 | Sodini et al. |
| 4,171,280 | A | 10/1979 | Maddox et al. |
| 4,435,601 | A | 3/1984 | Formanek et al. |
| 4,472,302 | A | 9/1984 | Karkhanis |
| 4,472,602 | A | 9/1984 | Bordelon et al. |
| 4,514,334 | A | 4/1985 | Mark |
| 4,623,465 | A | 11/1986 | Klibanov |
| 4,696,757 | A | 9/1987 | Blank et al. |
| 4,829,001 | A | 5/1989 | Mencke et al. |
| 4,900,671 | A | 2/1990 | Pokora et al. |
| 4,966,762 | A | 10/1990 | Pfeffer et al. |
| 5,141,611 | A | 8/1992 | Ford |
| 5,208,010 | A | 5/1993 | Thaler |
| 5,231,193 | A | 7/1993 | Mizusawa et al. |
| 5,260,021 | A | 11/1993 | Zeleznick |
| 5,296,376 | A | 3/1994 | Bridges et al. |
| 5,328,706 | A | 7/1994 | Endico |
| 5,389,369 | A | 2/1995 | Allen |
| 5,614,501 | A | 3/1997 | Richards |
| 5,653,746 | A | 8/1997 | Schmitt |
| 5,661,170 | A | 8/1997 | Chodosh |
| 5,700,769 | A | 12/1997 | Schneider et al. |
| 5,756,090 | A | 5/1998 | Allen |
| 5,824,414 | A | 10/1998 | Kobayashi et al. |
| 5,834,409 | A | 11/1998 | Ramachandran et al. |
| 5,839,369 | A | 11/1998 | Chatterjee et al. |
| 5,879,733 | A | 3/1999 | Ekanayake et al. |
| 5,891,440 | A | 4/1999 | Lansky |
| 6,068,862 | A | 5/2000 | Ishihara et al. |
| 6,080,573 | A | 6/2000 | Convents et al. |
| 6,136,849 | A | 10/2000 | Hoffmann et al. |
| 6,284,770 | B1 | 9/2001 | Mangel et al. |
| 6,383,523 | B1 | 5/2002 | Murad |
| 6,420,148 | B2 | 7/2002 | Yamaguchi |
| 6,436,342 | B1 | 8/2002 | Petri et al. |
| 6,444,805 | B1 | 9/2002 | Sohn et al. |
| 6,537,546 | B2 | 3/2003 | Echigo et al. |
| 6,551,602 | B1 | 4/2003 | Barrett et al. |
| 6,630,163 | B1 | 10/2003 | Murad |
| 6,642,277 | B1 | 11/2003 | Howard et al. |
| 6,926,881 | B2 | 8/2005 | Hirose et al. |
| 7,018,660 | B2 | 3/2006 | Murad |
| 7,241,461 | B2 | 7/2007 | Myhill et al. |
| 7,297,344 | B1 | 11/2007 | Fleischer et al. |
| 7,504,251 | B2 | 3/2009 | Olshenitsky et al. |
| 8,067,041 | B2 | 11/2011 | Quart et al. |
| 2002/0034553 | A1 | 3/2002 | Zayas |
| 2002/0041901 | A1 | 4/2002 | Murad |
| 2002/0172719 | A1 | 11/2002 | Murad |
| 2003/0078212 | A1 | 4/2003 | Li et al. |
| 2004/0137077 | A1 | 7/2004 | Ancira et al. |
| 2004/0228831 | A1 | 11/2004 | Belinka, Jr. et al. |
| 2005/0169988 | A1 | 8/2005 | Tao et al. |
| 2006/0024339 | A1 | 2/2006 | Murad |
| 2006/0024385 | A1 | 2/2006 | Pedersen |
| 2006/0051429 | A1 | 3/2006 | Murad |
| 2006/0165812 | A1* | 7/2006 | Charron ............... 424/600 |
| 2007/0010632 | A1 | 1/2007 | Kaplan et al. |
| 2007/0110812 | A1 | 5/2007 | Xia et al. |
| 2007/0154414 | A1 | 7/2007 | Bonfigillio |
| 2008/0118602 | A1* | 5/2008 | Narayanan et al. ........ 426/52 |
| 2009/0023804 | A1 | 1/2009 | Baugh et al. |
| 2009/0048312 | A1 | 2/2009 | Greenberg et al. |
| 2009/0083885 | A1 | 3/2009 | Daniell |
| 2009/0093440 | A1 | 4/2009 | Murad |
| 2010/0055138 | A1 | 3/2010 | Margulies et al. |
| 2010/0278759 | A1 | 11/2010 | Murad |

FOREIGN PATENT DOCUMENTS

| | | |
|---|---|---|
| EP | 1736165 | 12/2006 |
| WO | WO 94/03607 | 2/1994 |
| WO | WO 2004/003607 | 2/1994 |
| WO | WO 2006/038893 | 4/2006 |
| WO | WO 2007/003068 | 1/2007 |
| WO | WO 2010/018418 | 2/2010 |
| WO | WO 2010/101844 | 9/2010 |

OTHER PUBLICATIONS

U.S. Appl. No. 12/868,634, filed Mar. 1, 2010, Huang, et al.
U.S. Appl. No. 12/715,270, filed Mar. 1, 2010, Huang, et al.
U.S. Appl. No. 13/680,007, filed Nov. 16, 2012, Huang, et al.
U.S. Appl. No. 13/135,123, filed Jun. 24, 2011, Huang, et al.
U.S. Appl. No. 13/135,124, filed Jun. 24, 2011, Huang, et al.
U.S. Appl. No. 13/135,125, filed Jun. 24, 2011, Huang, et al.
U.S. Appl. No. 13/135,128, filed Jun. 24, 2011, Huang, et al.
U.S. Appl. No. 13/726,180, filed Dec. 23, 2012, Huang, et al.
U.S. Appl. No. 13/772,264, filed Feb. 20, 2013, Huang, et al.
Absolute Astronomy, Catechin, The Source of this article is Wikipedia,http://en.wikipedia.org/w/index.php?title=Catechin&oldid=77274034, Jan. 2008, 5 pages.
Akagawa et al., Production of Hydrogen Peroxide by Polyphenols and Polyphenol-rich Beverages UndeQuasi-physiological Conditions, Bioscience Biotechnol Biochem, 67(12), Sep. 2003, pp. 2632-2640.
Akiyama et al. Antibacterial Action of Several Tannins Against *Staphylococcus aureus*, Journal of Antimicrobial Chemotherapy, Jan. 2001, 48, pp. 487-491.
Aoshima et al., Antioxidative and Anti-hydrogen Peroxide Activities of Various Herbal Teas, Department of Chemistry, Faculty of Science, Yamaguchi University, 1677-1 Yoshida, Yamaguchi 753-8512, Japan, Available online Oct. 2, 2006, 1 page.
Bittner, When Quinones Meet Amino Acids: Chemical, Physical, and Biological Consequences, Amino Acids, Apr. 13, 2006, 30, pp. 205-224.
Blair, T.S., Botanic Drugs Their Materia Medica, Pharmacology and Therapeutics, The Therapeutic Digest Publishing Company, Cincnnati, Ohio, Jan. 1917, 20 pages.
Cheng, et al., Progress in Studies on the Antimutagenicity and Anticarcinogenicity of Green Tea Epicatechins, abstract, Chin. Med. Sci. J., Dec. 1991, 6(4), 1 page.
International Search Report for PCT/US2010/025805, Apr. 23, 2010, Metaactiv, Inc.
International Search Report for PCT/US2012/043900, Jan. 30, 2013, LiveLeaf, Inc.
Dayan et al., Oleic Acid-induced Skin Penetration Effects of a Lamellar Delivery System, excerpt (Cosmetics & Toiletries Magazine. Cosmetics and Toiletries.com, http://www.cosmeticsandtoiletries.com/formulating/ingredientldelivery/9496857.html, Aug. 31, 2007, 2pages.
Definition of "Compound" and "Composition", Grant and Hackh's Chemical Dictionary, 5$^{th}$ Ed. McGraw Hill, 1987, 2 pages.
Del Rio, D., et al., HPLC-MS$^n$ Analysis of Phenolic Compounds and Purine Alkaloids in Green and Black Tea, J Agric Food Chem, 2004, 52, pp. 2807-2815.
Do-It-Yourself Health, Editor: R. Somerville, Time Life Books, 1997, 2 pages.
Dudley et al., Cysteine as an Inhibitor of Polyphenol Oxidase, abstract, Journal of Food Biochemistry. Feb. 23, 2007,13(1), 1 page.
Feldman et al,. Binding Affinities of Gallotannin Analogs with Bovine Serum Albumin: Ramifications for Polyphenol-protein Molecular Recognition, Phytochemistry Jan. 1999, 51, Elsevier Science Ltd., pp. 867-872.
Gallochem Co., Ltd., Gallotannin, http://www.gallochem.com/Gallochem I.htm, Jan. 2002, 4 pages.
Goel et al., Xylanolytic Activity of Ruminal *Streptococcus bovis* in Presence of Tannic Acid, Annals of Microbiology, Jan. 2005, 55(4), pp. 295-297.
Grabber, Mechanical Maceration Divergently Shifts Protein Degradability in Condensed-Tannin vso-Quinone Containing Conserved Forages, Crop Science, Mar. 19, 2008, 48, 2 pages.
greentealovers.com, Green Tea, White Tea: Health Catechin,http://greentealovers.com/greenteahealthcatechin.htm#catechin, Accessed Feb. 9, 2010, pp. 1-13.

(56) References Cited

OTHER PUBLICATIONS

Guo et al., Studies on Protective Mechanisms of Four Components of Green Tea Polyphenols Against Lipid Peroxidation in Synaptosomes, abstract, Biochim. Biophys. Acta Dec. 13, 1996, 1304(3), 1 page.

Guo, et al., Evaluation of Antioxidant Activity and Preventing DNA Damage Effect of Pomegrante Extracts by Chemiluminescence Method, J Agric Food Chem, 2007, 55, pp. 3134-3140.

Hagerman, Tannin Chemistry, Oxford, OH, Jan. 1998, 116 pages.

Hasson, et al., Protein Cross-linking by Peroxidase: Possible Mechanism for Sclerotization of Insect Cuticle, abstract Archives of Insect Biochemistry and Physiology, Dec. 16, 1986, 1 page.

Ho, et al., Antioxidative Effect of Polyphenol Extract Prepared from Various Chinese Teas, abstract Prev. Med .Jul. 1992, 21(4), 1 page.

Ishiguro et al., Effects of Conjugated Linoleic Acid on Anaphylaxis and Allergic Pruritus,Biol. Pharm. Bull., Dec. 2002, 25(12), pp. 1655-1657.

Ishikawa et al Effect of Tea Flavonoid Supplementatation on the Susceptibility of Low-density Lipoprotein to Oxidative Modification, abstract, Am J Clin Nutr, Aug. 1997, 66(2), 1 page.

Kabara, J.J., et al., Fatty Acids and Derivatives as Antimicrobial Agents, Antimicrobial Agents and Chemotherapy, 2(1), Jul. 1972, pp. 23-28.

Kamin et al., Stimulation by Dinitrophenol of Formation of Melanin-like Substance from Tyrosine by Rat Liver Homogenates, The Journal of Biological Chemistry, downloaded from www.jbc.org, on Oct. 31, 2008, pp. 735-744.

Kashiwada et al., Antitumor Agents, 129. Tannins and Related Compounds as Selective Cytotoxic Agents, abstract, J Nat Prod, Aug. 1992, 55(8), 1 page.

Kilic et al., Fatty Acid Compositions of Seed Oils of Three Turkish Salvia Species and Biological Activities, Chemistry of Natural Compounds, 41(3), Jan. 2005, Springer Science+Business Media, Inc., pp. 276-279.

Kim, et al., Effect of Glutathione, Catechin and Epicatechin on the Survival of *Drosophilia melanogaster* Under Paraquat Treatment, abstract, Biosci. Biotechnol Biochem, Feb. 1997 ,61(2), 1 page.

Kim, et al., Research Note: Antimicrobial Effect of Water-Soluble Muscadine Seed Extracts on *Escherichia coli* 0157-H7, abstract, Journal of Food Protection, 71(7), Jul. 2008, 1 page.

Kim, et al., Measurement of Superoxide Dismutase-like Activity of Natural Antioxidants, abstract, Viosci Biotechnol Biochem, May 1995, 59(5), 1 page.

Krab-Husken, L., Production of Catechols, Microbiology and Technology, Thesis Wageningen University, The Netherlands, Jan. 2002, ISBN 90-5808-678-X, pp. 9-144.

Labieniec, M., et al., Study of Interactions Between Phenolic Compounds and $H_2O_2$ or Cu(II) Ions in B14 Chinese Hamster Cells, Cell Biology Int'l, 2006, 30, pp. 761-768.

Lee et al., Antimicrobial Synergistic Effect of Linolenic Acid and Monoglyceride Against *Bacillus cereus* and *Staphylococcus* Journal of Agricultural and Food Chemistry, Jan. 2002, 50, pp. 2193-2199.

Li, W-Z., et al.., Stabilizing the Bactericidal Activity of Hydrogen Peroxide: A Brandnew Function of Certain Chinese Herbs, Chin J Integr Med, Dec. 3, 2012, 6 pages.

Lotito et al., Catechins Delay Lipid Oxidation and α-Tocopherol and β-Carotene Depletion Following Ascorbate Depletion in Human Plasma, Society for Experimental Biology and Medicine, Apr. 2000, pp. 32-38.

MacPhillamy, HB., Drugs from Plants, Plant Science Bulletin, Apr. 1963, 9(2), pp. 1-15.

Maffei, et al., Relevance of Apple Consumption for Protection Against Oxidative Damage Induced by Hydrogen Peroxide in Human Lymphocytes; The British Journal of Nutrition, Cambridge, 97(5), May 2007, pp. 921-928.

Matsumoto et al. Inhibitory Effects of Tea Catechins, Black Tea Extract and Oolong Tea Extract on Hepatocarcinogenesis in Rat, abstract, Jpn. J. Cancer Res., Oct. 1996, 87(10), 1 page.

Morris et al.Affinity Precipitation of Proteins by Polyligands, http://www.ncbi.nlm.nih.gov/pubmed/18601281. Biotechnol Bioeng, Apr. 25, 1993, 41(10), 1 page.

Nanjo et al., Scavenging Effects of Tea Catechins and Their Driviatives on 1, 1-diphenyl-2-picrythydrazyl Radical, abstract free Radic. Bioi. Med .Jan. 1996, 2I(6), 1page.

Obermeier et al., Effects of Bioflavonoids on Hepatic P450 Activities, abstract, Xenobiotica, Jun. 1995, 25(6), 1 page.

OMEGA-3 Fatty Acids, University of Maryland Medical Center, http://www.umm.edulaltmedlarticles/omeza-3-000316.htm accessed Feb. 12, 2010.

Parrish, Jr. et al., Effects of Conjugated Linoleic Acid (CLA) on Swine Performance and Body Composition, Jan. 1998/997 Swine Research Report, Iowa State University, AS-638, pp. 187-190.

Poyrazoglu, E., et al., Organic Acids and Phenolic Compounds in Pomegranates (*Punica granatum* L.) Grown in Turkey, J Food Comp Analysis, 2002, 15, pp. 567-575.

Preuss, H.G., et al., Minimum Inhibitory Concentrations of Herbal Essential Oils and Monolaurin for Gram-positive and Gram-negative Bacteria, Molecular and Cellular Biochemistry, Jan. 2005, 272, pp. 29-34.

Prottey et al., The Mode of Action of Ethyt Lactate as a Treatment for Acne, British Journal of Dermatology, 110(4), Jul. 29, 2006.

Raskin, et al., Can an Apple a Day Keep the Doctor Away?, Current Pharmaceutical Design, 2004, 10, pp. 3419-3429.

Roginsky et al., Oxidation of Tea Extracts and Tea Catechins by Molecular Oxygen, abstract, Journal of Agricultural Food Chemistry, 52(II), Apnl 30, 2005, 1 page.

Rucker et al, Copper, Lysyl Oxidase, and Extracellular Matrix Protein Cross-linking, The American Journal of Clinical Nutrition, '67(suppl.), Jan. 1998, pp. 996S-1002S.

Sachinidis et al., Are Catechins Natural Tyrosine Kinase Inhibitors? Drug News & Perspectives, Jan. 2002, 15(7), 432, ISSN 0214-0934, 1 page.

Sasaki, et al., Ecabet Sodium Prevents the Delay of Wound Repair in Intestinal Epithelial Cells Induced by Hydrogen Peroxide, J. Gastroenterol, 40, 2005, pp. 474-482.

Sato, et al., Ammonia Hydrogen Peroxide, and Monochloramine Retard Gastric Epithelial Restoration in Rabbit Cultured Cell Model, Digestive Diseases and Sciences, New York, 44(12), Dec. 1, 1999, pp. 2429-2434.

Schweikert et al., Scission of Polisaccharides by Peroxidase-Generated Hydroxyl Radicals, Phytochemistry, 53(5), Mar. 1, 2000, 2 pages.

Scott, et al., Evaluation of the Antioxidant Actions of Ferulic Acid and Catechins, abstract, Free Radic Res Commun, Jan. 1993, 19(4), 1 page.

Sebedio, J-L, et al., Vegetable Oil Products, Advances in Conjugated Linoleic Acid Research, Jan. 2003, 2, Urbana, IL, 2 pages.

Selinheimo, Tyrosinase and Laccase as Novel Crosslinking Tools for Food Biopolymers,http:/lib.tkk.fi/Diss/2008/isbn9789513871185/index.html, age last updated: Feb. 2, 2010, Page maintained by: diss@tkk, fi, 5 pages.

Stapleton et al., Potentiation of Catechin Gallate-Mediated Sensitization of *Staphylococcus aureus* to Oxacillin by Nongalloylated Catechins, Antimicrobial Agents and Chemotherapy, Feb. 2006, pp. 752-755.

Stark, D., et al., Irritable Bowel Syndrome: A Review of the Role of Intestinal Protozoa and the Importance of their Dectection and Diagnosis, Intl J Parasitology, 2007, 37, pp. 11-20.

Steele, et al., Chemopreventive Efficacy of Black and Green Tea Extracts in Vitro Assays, meeting abstract, Proc Annu Meet Am Assoc Cancer Res, Jan. 1996, 37, 1 page.

Terao et al., Protective Effect of Epicatechin, Epicatechin Gallate, and Quercetin on Lipid Peroxidation in Phospholipid Bilayers, abstract; Arch Biochem Biophys, Jan. 1994, 308(1), 1 page.

Tomisato, et al., Maturation Associated Increase in Sensitivity of Cultured Guinea Pig Gastric Pit Cells to Hydrogen Peroxide, Digestive Diseases and Sciences, New York, Sep. 2002, 47(9), pp. 212-2132.

Uyama et al., Enzymatic Synthesis and Properties of Polymers from Polyphenols, Advances in Polymer Science, Jan. 2006, 194, ISSN 0065-3195, 1 page.

Valcic et al., Inhibitory Effect of Six Green Tea Catechins and Caffeine on the Growth of Four Selected Human Tumor Cell Lines, abstract, Anticancer Drugs, Jun. 1996, 7(4),1 page.

(56) References Cited

OTHER PUBLICATIONS

Varghese et al., Effect of Asoka on the Intracellular Glutathione Levels and Skin Tumor Promotion in Mice, abstract, Cancer Lett, Apr. 15, 1993, 69(1), 1 page.
Vermerris, W., et al., Phenolic Compound Biochemistry, Springer, 2008, 13 pages.
Wikipedia, Tannin, http://en.wikipedia.org/wiki|Tannin, This page was last modified on Jan. 30, 2010, 35 pages.
Wu-Yuan et al., Gallotannins Inhibit Growth, Water-insoluble Glucan Synthesis, and Aggregation of Mutans Streptococci, J Dent Res, Jan. 1988, 67(1), pp. 51-55.
Yamamoto et al., Studies on Quinone Cross-linking Adhesion Mechanism and Preparation of Antifouling Surfaces Toward the Blue Mussel, abstract, Journal of Marine Bitechnology, 5(2-3), May 1997, 1 page.
Yokozawa, T., et al., Effects of Rhubarb Tannins on Renal Function in Rats with Renal Failure, abstract, Nippon Jinzo Gakkai Shi, Jan. 1993, 35(1), 1 page.
Yoshino et al., Antioxidative Effects of Black Tea Theaflavins and Thearubigin on Lipid Peroxidation of Rat Liver Homogenates Induced by Tert-butyl Hydroperoxide, abstract, Biol Pharm Bull, Jan. 1994, 17(1), 1 page.
Zhang et al., Inhibitory Effects of Jasmine Green Tea epicatechin Isomers on Free Radical-induced Lysis of Red Blood Cells, abstract Life Sci, Jan. 1997, 61(4), 1 page.
Zhu et al., Antioxidant Chemistry of Green Tea Catechins: Oxidation Products of (−)- Epigallocatechin Gallate and (−)- With Peroxidase, Wiley InterScience Journals: Journal of Food Lipids, May 5, 2007, 7(4), 1 page.
Agnivesa, Caraka Samhita, Edited & translated by P.V. Sharma, vol. II: Chaukhamba Orientalia, Varanasi, Edn. $5^{th}$, 2000. [time of origin 1000 BC—$4^{th}$ century] p. 418.
Asquith, T.N., et al., Interactions of Condensed Tannins with Selected Proteins, Phytochemistry, 1986, 25, pp. 1591-1593.
Avdiushko, S.A., et al., Detection of Several Enzymatic Activities in Leaf Prints of Cucumber Plant, Physiological and Molecular Plant Pathology, 1993, 42, pp. 441-454.
Baeuerle, P.A., Reactive Oxygen Intermediates as Second Messengers of a General Pathogen Response, Pathol Biol., 1996, 44(1), pp. 29-35.
Barroso, J.B., et al., Localization of Nitric-oxide Synthase in Plant Peroxisomes, The Journal of Biological Chemistry, 1999, 274(51), pp. 36729-36733.
Berglin, E.H., et al., Potentiation by L-Cysteine of the Bactericidal Efffect of Hydrogen Peroxide in *Escherichia coli*, J. Bacteriol., 1982, 152(1), pp. 81-88.
Berglin, E. H., et al., Potentiation by Sulfide of Hydrogen Peroxide-Induced Killing of *Escherichia coli*, Infection and Immunity, 1985, 49(3), pp. 538-543.
Bernays, E.A., et al., Herbivores and Plant Tannins, Advances in Ecological Research, 1989, 19, pp. 263-302.
Bowditch, M.I., et al., Ascorbate Free-Radical Reduction by Glyoxysomal Membranes, Plant Physiology, 1990, 94, pp. 531-537.
Bowler, C., et al., Superoxide Dismutase and Stress Tolerance, Annu Rev Plant Physiol Plant Mol Biol, 1992, 43, pp. 83-116.
Bowler, C., et al., Superoxide Dismutase in Plants, Crit Rev Plant Sci, 1994, 13(3), pp. 199-218.
Breusegem, F.V., et al., The Role of Active Oxygen Species in Plant Signal Transduction, Plant Science, 2001, 161, pp. 405-414.
Buchanan-Wollaston, V., The Molecular Biology of Leaf Senescence, 1997, J. Exp. Bot, 48(2), pp. 181-199.
Bunkelmann, J.R., et al., Ascorbate Peroxidase. A Prominent Membrane Protein in Oilseed Glyoxysomes, 1996, Plant Physiol.,110(2), pp. 589-598.
Butler, E., et al., The role of Lysyl Oxidase and Collagen Crosslinking During Sea Urchin Development, Exp Cell Res, 1987, 173, pp. 174-182.
Butler, L.G., et al., Interaction of Proteins with Sorghum Tannin: Mechanism, Specificity and Significance, Journal of the American Oil Chemists' Society, 1984, 61(5), pp. 916-920.
Chemtutor Solutions, [online] http://www.chemtutor.com/solution.htm, 11 pages. May 8, 1998, [retrieved from the internet archive Wayback Machine using internet URL http://wayback.archive.org/web/*/http://www.chemtutor.com/solution.htm].
Cheng, H.Y., et al., Antiherpes Simplex Virus Type 2 activity of Casuarinin from the Bark of *Terminalia arjuna* Linn, Antiviral Research, 2002, 55(3), pp. 447-455.
Cordeiro, C., et al., Antibacterial Efficacy of Gentamicin encapsulated in pH-Sensitive Liposomes against an In Vivo *Salmonella* enteric Serovar Typhimurium Intracelllular Infection Model, Antimicrobial agents and Chemotherapy, 2000, 44(3), pp. 533-539.
Corpas, F.J., et al., A Role for Leaf Peroxisomes in the Catabolism of Purines, 1997, J. Plant Physiol, 151, pp. 246-250.
Corpas, F.J., et al., Copper-Zinc Superoxide Dismutase is a Constituent Enzyme of the Matrix of Peroxisomes in the Cotyledons of Oilseed Plants, New Phytol, 1998, 138(2), pp. 307-314.
Daayf et al, Recent Advances in Polyphenol Research, 2008, Blackwell Publishing, p. 264 (3 pages).
De Paepe, K., et al., Repair of Acetone and Sodium Lauryl Sulphate-Damaged Human Skin Barrier Function Using Topically Applied Emulsions Containing Barrier Lipids, abstract, Journal of European Academy of Dermatology & Venereology, Nov. 2002, 1 page.
Del Río, L.A., et al., Metabolism of Oxygen Radicals in Peroxisomes and Cellular Implications, Free Radical Biol Med, 1992, 13(5), pp. 557-580.
Del Río, L.A., et al., Peroxisomes as a Source of Superoxide and Hydrogen Peroxide in Stressed Plants, Biochem Soc Trans, 1996, 24, pp. 434-438.
Del Rio, L.A., et al., The Activated Oxygen Role of Peroxisomes in Senescence, Plant Physiol., 1998, 116(4), pp. 1195-1200.
Doke, N., et al., The Oxidative Burst Protects Plants Against Pathgen Attack: Mechanism and Role as an Emergency Signal for Plant Bio-Defence, Gene, 1996, 179(1), pp. 45-51.
El Amin, F.M., et al., Genetic and Environmental Effects upon Reproductive Performance of Holstein Crossbreds in the Sudan, Dairy Sci, 1986, 69, pp. 1093-1097.
Elstner, E.F., et al., Mechanisms of Oxygen Activation During Plant Stress, Proceedings of the Royal Society of Edinburgh B Biology, 1994, 102B, pp. 131-154.
Fang, T.K., et al., Electron Transport in Purified Glyoxysomal Membranes from Castor Bean Endosperm, Planta, 1987, 172(1), pp. 1-13.
Fridovich, I., Superoxide Dismutases, Adv Enzymol Relat Areas Mol Biol, 1986, 58, pp. 61-97.
Funatogawa, K., et al., Antibacterial Activity of Hydrolysable Tannins Derived from Medicinal Plants against *Helicobacter pylori*, Microbiol Immunol, 2004, 48(4), pp. 251-261.
Gallily, R., et al., Non-immunological Recognition and Killing of Xenogeneic Cells by Macrophages. III. Destruction of Fish Cells by Murine Macrophages, Dev Comp Immunol., 1982 Summer, 6(3), pp. 569-578.
Gan, S., et al., Making Sense of Senescence. Molecular Genetic Regulation and Manipulation of Leaf Senescence, Plant Physiol., 1997, 113, pp. 313-319.
Hagerman, A.E., et al., The Specificity of Proanthocyanidin-Protein Interactions, Journal of Biological Chemistry, 1981, 256(9), pp. 4494-4497.
Hagerman, A.E., et al., Specificity of Tannin-Binding Salivary Proteins Relative to Diet Selection by Mammals, Canadian Journal of Zoology, 1992, 71, pp. 628-633.
Halwani, M., et al., Bactericidal Efficacy of Liposomal Aminoglycosides against *Burkholderia cenocepacia*, Journal of Antimicrobial Chemotherapy, 2007, 60, pp. 760-769.
Heber, Multitargeted therapy of cancer by ellagitannins, 2008, Cancer Letters, 269,pp. 262-268.
Jiménez, A., et al., Evidence for the Presence of the Ascorbate-Glutathione Cycle in Mitochondria and Peroxisomes of Pea Leaves, Plant Physiol., 1997, 114(1), pp. 275-284.
Jiménez, A., et al., Ascorbate-Glutathione Cycle in Mitochondria and Peroxisomes of Pea Leaves: Changes Induced by Leaf Senescence, Phyton, 1997, 37, pp. 101-108.

(56) References Cited

OTHER PUBLICATIONS

Kolodziej, H., et al., Antileishmanial Activity and Immune Modulatory Effects of Tannins and Related Compounds on Leishmania Parasitised RAW 264.7 Cells, Phytochemistry, 2005, 66(17), pp. 2056-2071.

Kahn, Khazaain-al-advia, vol. II (20$^{th}$ century AD), Nadeem Yunas Printer/Sheikh Mohd Basheer & Sons, Lahore, 1911 p. 611.

Kuboe, et al., Quinone cross-Linked Polysaccharide Hybrid Fiber, Biomacromolecules, 2004, 5(2), pp. 348-357.

Lagrimini, L.M., Wound-Induced Deposition of Polyphenols in Transgenic Plants Overexpressing Peroxidase, Plant Physiol, 1991, 96, pp. 577-583.

Lamb, C., et al., The Oxidative Burst in Plant disease Resistance, Annu Rev Plant Physiol Mol Bio, 1997, 48, pp. 251-275.

Landolt, R., et al., Glyoxysome-like Microbodies in Senescent Spinach Leaves, Plant Sci., 1990, 72(2), pp. 159-163.

Lane, B.G., Oxalate Oxidases and Differentiating Surface Structure in Wheat: Germins, Biochem J., 2000, 349, pp. 309-321.

Li, J., et al., Hydrogen Peroxide and Ferulic Acid-Mediated Oxidative Cross-linking of Casein catalyzed by Horseradish Peroxidase and the Impacts on Emulsifying Property and Microstructure of Acidified Gel, African Journal of Biotechnology, 2009, 8(24), pp. 6993-6999.

Lin, C.C., et al., Hydrogen Peroxide Level and NaCl-inhibited Root Growth of Rice Seedlings, Plant and Soil, 2001, 230, pp. 135-143.

López-Huertas, E., et al., Superoxide Generation in Plant Peroxisomal Membranes: Characterization of Redox Proteins Involved, Biochem. Soc. Trans., 1996, 24, 195S.

López-Huertas, E., et al., Superoxide Radical Generation in Peroxisomal Membranes: Evidence for the Participation of the 18-kDa Integral Membrane Polypeptide, Free Radical Res., 1997, 26(6), pp. 497-506.

Lopez-Huertas, E., et al., Stress Induces Peroxisome Biogenesis Genes, The EMBO Journal, 2000, 19(24), pp. 6770-6777.

Low, P.S., et al., The Oxidative Burst in Plant Defense: Function and Signal Transduction, Physiologia Plantarum, 1996, 96(3), pp. 533-542.

Lu, L., et al., Tannin Inhibits HIV_1 Entry by Targeting gp41, Acta Pharmacol Sin, Feb. 2004, 25(2), pp. 213-218.

Luster, D.G., et al., Orientation of Electron Transport Activities in the Membrane of Intact Glyoxysomes Isolated from Castor Bean Endosperm, Plant Physiol, 1987, 85, pp. 796-800.

Matile, P., et al., Chlorophyll Breakdown in Senescent Leaves, Plant Physiol., 1996, 112(4), pp. 1403-1409.

Mohammad.Bin Zakariyya Al-Razi; Kitaab-al-Haawi-fil-Tibb, vol. IX (9$^{th}$ century A.D.), Dayerah-al-Ma'aarif Usmania, Hyderabad, (First Edition) 1960 p. 194.

Mohammad.Bin Zakariyya Al-Razi; Kitaab-al-Haawi-fil-Tibb, vol. XX (9$^{th}$ century A.D.), Dayerah-al-Ma'aarif Usmania, Hyderabad, (First Edition) 1967 p. 226.

Mohammadi, M., et al., Changes in Peroxidase and Polyphenol activity in Susceptible and Resistant Wheat Heads Inoculated with fusarium Granminearum and Induced Resistance, Plant Science, 2002, 162, pp. 491-498.

Mugabe, C., et al., Mechanism of Enhanced Actibvity of Liposoome-entrapped Aminoglycosides Against Resistant Strains of *Pseudomonas aeruginosa*, Antimicrob. Agents Chemother., 2006, 50, pp. 2016-2022.

Narayanan, B., et al., p53/p21 (WAF1/CIP1) Expression and Its Possible Role in G1 Arrest and Apoptosis in Ellagic Acid Treated Cancer Cells, Cancer Letters, 1999, 136, pp. 215-221.

Nishimura, M., et al., Leaf peroxisomes are Directly Transformed to Glyoxysomes During Senescence of Pumpkin Cotyledons, Protoplasma, 1993, 175(3-4), pp. 131-137.

Nonaka, G-I., et al., Anti-AIDS Agents, 2: Inhibitory Effects of Tannins on HIV Reverse Transcriptase and HIV Replication in H9 Lymphocyte Cells, J. Natl. Prod., 1990, 53(3), pp. 587-595.

Orozco-Cardenas, M., et al., Hydrogen Peroxide is Generated Systematically in Plant Leaves by Wounding and Systemin via the Octadecanoid Pathway, Proc. Natl. Acad. Sci. USA, May 1999, 96, pp. 6553-6557.

Pastori, G.M., et al., An Activated-Oxygen-Mediated Role for Peroxisomes in the Mechanism of Senescence of *Pisum sativum*, Planta, 1994, 193(3), pp. 385-391.

Pastori, G.M., et al., Activated Oxygen Species and Superoxide Dismutase Activity in Peroxisomes from Senescent Pea Leaves, Proc R Soc Edinb Sect B Biol, 1994, 102B, pp. 505-509.

Pastori, G.M., et al., Natural Senescence of Pea Leaves: an Activated Oxygen-Mediated Function for Peroxisomes, Plant Physiol., 1997, 113(2), pp. 411-418.

Pistelli, L., et al., Glyoxylate Cycle Enzyme Activities are Induced in Senescent Pumpkin Fruits. Plant Sci., 1996, 119(1-2), pp. 23-29.

Pryor, M.G.M., On the Hrdening of the Ootheca of Blatta Orientalis, Soc Lond Ser B, 1940, 128, pp. 378-393.

Quideau, S., et al., Main Structural and Stereochemical Aspects of the Antiherpetic Activity of Nonahydroxyterphenoyl-Containing C-Glycosidic Ellagitannins, Chemistry and Biodiversity, 2004, 1(2), pp. 247-258.

Ratnakara, Complied by Naginadasa Chaganalala Saha, Translated by Gopinath Gupta, vol. V: B. Jain Publishers, New Delhi, Edn. 2$^{nd}$ Reprint, Aug. 1999.[This book contains back references from 1000 B.C. to 20 th century] p. 736.

Ray, H., et al., Transformation of Potato with Cucumber Peroxidase: Expression and disease Response, Physiological and Molecular Plant Pathology, 1998, 53, pp. 93-103.

Robertson, J.A., et al., Peroxidase-Mediated Oxidative Cross-Linking and Its Potential to Modify Mechanical Properties in Water-Soluble Polysaccharide Extracts and Cereal grain Residues, abstract, J Agric Food Chem, 2008, 56(5), 1 page.

Smart, C.M., Gene Expression During Leaf Senescence, New Phytol, 1994, 126(3), pp. 419-448.

Smkaradajisastripade: Aryabhisaka- Gujarati Edited (Hindustana No Vaidyaraja) Translation by Harikrishna Bhagwan Lal Vyas: Sastu Sahitya Vardhaka Karyalaya, Bhadra, Ahmedabad, Edn. 12$^{th}$, 1957 p. 92.

Stachowicz, J.J., et al., Reducing Predation Through Chemically Mediated Camouflage: Indirect Effects of Plant Defenses on Herbivores, Ecology, 1999, 80(2), pp. 495-509.

Stahmann, M.A., et al., Cross Linking of Proteins In Vitro by Peroxidase, Biopolymers, 16(6), pp. 1307-1318.

Sugumaran, M., Comparative Biochemistry of Eumelanogenesis and the Protective Roles of Phenoloidase and Melamin in Insects, Pigment Cell Res., 2002, 15(1), pp. 2-9.

Tanimura, S., et al., Suppression of Tumor Cell Invasiveness by Hydrolyzable Tannins (Plant Polyphenols) via the Inhibition of Matrix Metalloproteinase-2/-9 Activity, Biochemical and Biophysical Research Communications, 2005, 330, pp. 1306-1313.

Thompson, J.E., et al., Tansley Review No. 8. The Role of Free Radicals in Senescence and Wounding, New Phytol, 1987, 105, pp. 317-344.

Van Den Bosch, H., et al., Biochemistry of Peroxisomes, Annu. Rev. Biochem., 1992, 61, pp. 157-197.

Vangasena, Commentator Shaligram Vaisya, Edited Shankar Lalji Jain:Khemraj Shrikrishna Das Prakashan, Bombay, Edn. 1996 p. 1046.

Wang, S.X., et al., A crosslinked Cofactor in Lysyl Oxidase: Redox Function for Amino Acid Side Chains, Science, 1996, 273(5278), pp. 1078-1084.

Weiss, et al., Review: Conjugated Linoleic Acid: Historical Context and Implications 1, Professional Animal Scientist, Apr. 2004, 29 pages.

Wiechers, J.W., Nutraceuticals and Nanoparticles, Cosmetics & Toiletries Magazine, CosmeticsAndToiletries.com, http://www.cosmeticsandtoiletries.com/research/techtransfer/9431641.html?page=4, Aug. 28, 2007.

Willekens, H., et al., Catalase is a Sink for $H_2O_2$ and is Indispensable for Stress Defense in $C_3$ Plants, The EMBO Journal, 1997, 16(16), pp. 4806-4816.

(56) References Cited

OTHER PUBLICATIONS

Wikipedia, Tannin, http://en.wikipedia.org/wiki/Tannin, This page was last modified on Jan. 30, 2010, 35 pages, accessed on Jan. 4, 2011.

Woo, E.-J., et al., Germin is a Manganese Containing Homohexamer with Oxalate Oxidase and Superoxide Dismutase Activities, Nature Structural Biology, 2000, 7(11), pp. 1036-1040.

Yamaguchi, K., et al., A Novel Isoenzyme of Ascorbate Peroxidase Localized on Dlyoxysomal and Leaf Peroxisomal Membranes in Pumpkin, Plant Cell Physiol., 1995, 36(6), pp. 1157-1162.

Yamamoto et al., Roles of Catalase and Hydrogen Peroxide in Green Tea Polyphenol-Induced Chemopreventive Effects, Journal of Pharmacology and Experimental Therapeutics Fast forward, 2003, 32 Pages, DOI:10.1124/jpet.103.058891, JPET #58891.

Yang, L-L., et al., Induction of Apoptosis by Hydrolyzable Tannins from *Eugenia jambos* L. on Human Leukemia Cells, Cancer Letters, 2000, 157, pp. 65-75.

Hara et al., Antioxidative Effects of Black Tea Theaflavins and Thearubigin on Lipid Peroxidation of Rat Liver Homogenates Induced by Tert-butyl Hydroperoxide, abstract, Biol Pharm Bull, Jan. 1994, 17(1), 1 page.

Ziya Al-Din Abdullah Ibn Al-Baitar: Al-Jaam'e-li-Mufradaat-al-Advica-wal-Aghzia, vol. 1 (13th century AD), Matba Amra, Cairo, Egypt, 1874 A.D. p. 162.

Zheng, C.J., et al., Fatty Acid Synthesis is a Target for Antibacterial Activity of Unsaturated Fatty Acids, FEBS Letters, 2005, 579, pp. 5157-5162.

\* cited by examiner

THERAPEUTIC COMPOSITION PRODUCED USING *CAMELLIA SINENSIS* LEAVES AND HYDROGEN PEROXIDE

CROSS-REFERENCE TO RELATED APPLICATIONS

This application is a continuation of U.S. patent application Ser. No. 12/715,270, filed Mar. 1, 2010, now U.S. Pat. No. 8,343,552, which claims the benefit of U.S. Provisional Application Ser. No. 61/209,260, filed Mar. 4, 2009, and is a continuation-in-part of U.S. patent application Ser. No. 12/317,638, filed Dec. 23, 2008, which claims the benefit of U.S. Provisional Patent Application Ser. No. 61/009,484, filed Dec. 28, 2007; each application of which is hereby incorporated herein by reference.

FIELD OF INVENTION

The present invention generally relates to controlled enhancement of protein binding affinity of biomaterials. More in particular, the invention relates to stabilization of and controlled activation of plant biopolymers by enzymes of animals, plants, bacteria, and/or other catalysts to cause locally enhanced oxidation and/or cross-linking of proteins, micro-organisms and biologic tissues.

BACKGROUND OF THE INVENTION

Despite hundreds of millions of years of divergent evolution, almost all plants, animals and pathogens share some common biochemical fundamentals and strategies for environmental defense. This makes botany a rich source of useful and compatible compounds for the control of pathogens in animals. The use of functional biochemistry from the plants has long been the basis for traditional and herbal medicines and often considered less likely to trigger unwanted immunological responses between less genetically distant species within the same phyla than highly purified large complicated proteins or polymers.

Immune systems of most of the higher organisms protect from infection with defenses of increasing specificity. The simplest is a physical barrier that prevents pathogens, such as bacteria and viruses, from entering the organism. Plants and animals also have innate immune systems that are either genetically coded responses to specific pathogens, or various non-specific responses to pathogen chemistries.

Plants typically have a two branched immune system. The first recognizes and responds to molecules common to many classes of microbes, including non-pathogens, by increased expression of ROS (Reactive Oxygen Species) generating enzymes capable of initiating oxidative bursts, but such direct oxidative response is energy costly and must be strictly regulated to prevent autotoxicity. Many pathogenic microorganisms (bacteria, fungi, protozoa) are equipped with peroxidases or catalases as countermeasures against such ROS bursts. The second branch of the innate immune system is the multi-component wound response as described above initiated by the reaction between quinonic compounds and amino acids when cells are damaged. These compounds are usually compartmentally separated and do not cooperate in living systems. In plants, cellular disruption causes various phenol compounds and reactive oxygen species to come into contact with polyphenol oxidases (PPO), oxidizing the phenol compounds to form quinonic compounds that aggressively associate with each other and amino acids of the cells or any microorganisms present. This effects many physiologic phenomena, such as browning or discoloring of foods, precipitation of proteins, germicidal activity, astringency, changes in food digestibility and more.

Polyphenol oxidation in plant systems generates oxidized-polyphenols (also referred to as o-polyphenols, oxidized biopolymers, polyquinones and quinonic compounds) with a multiplicity of quinonic groups that are capable of covalent bonding. Once formed, the high affinity o-polyphenols spontaneously form covalent intra- and inter-chain cross-links that condense proteins far more aggressively than hydrogen bonds characteristic of non-oxidized polyphenols. In plant systems, o-polyphenols cross link damaged cell proteins to form a refractory shield between the healthy tissues and further assault. They also prevent pathogen propagation by aggressively binding to their metabolic pathways, disabling virulence enzymes and arresting pathogen motility.

Higher vertebrates possess an additional layer of protection, the adaptive immune system, which allows for a stronger immediate immune response to previously encountered pathogens. The aggregation of smaller molecules on the pathogen creates large complexes with an increased antigenicity of the pathogen to the host immune system. Each pathogen is "remembered" by a signature antigen. Should a pathogen infect the body more than once, these specific memory cells are used to quickly and efficiently eliminate it; however, these tailored responses can take many days to develop. In the interim, primary defense against newly encountered pathogens, especially in infection of immunologically deficient or immature animals relies solely on the innate immune systems and often is associated with negative physiologic responses such as diarrhea, vomiting, fever, inflammation, etc. Such systemic responses to infection are the expression of the very large numbers of immune effectors that can be extremely metabolically expensive, even fatal to the host.

One of the most common dangers associated with an unchecked systemic response by the innate immune system is diarrheal dehydration triggered by infectious diseases or parasites. Diarrheal dehydration affects over 2 billion people each year and is the most common cause of death for Third World infants, responsible for over 1.5 million deaths per year. Besides re-hydration, most efforts to treat diarrhea have focused on increasing human mucosal immunity by modulating systemic immune responses, such as by using intestinal motility reducing drugs, mucous permeability modifiers or antibiotic therapies. These approaches have limited success but introduce undesirable risks of side effects, pathogen resistance, or physiologic senescence.

There is constant commercial demand for botanical alternatives to antibiotics and synthetic chemical disinfectants for the control of disease associated with water, surface, and food borne pathogens. The explosive rise in antibiotic resistant diseases has been associated with the overuse of antibiotics in both humans and livestock. Many regional governments and international health organizations have called for phase out of unnecessary antibiotic use, especially in livestock feeds where they are used sub-therapeutically to enhance growth. To date, it is widely recognized that there are few cost effective and environmentally sound alternatives for the safe control of pathogens. Decades of research on plants as sources of new antimicrobials has primarily focused on mechanical or solvent extraction of specific plant compounds and has not been successful in generating compositions with potency, safety, user preference and environmental profile necessary to match the performance of current antibiotics and germicides.

SUMMARY OF THE INVENTION

In an aspect, a biochemical composition comprises a processed fluid containing a molecule having a hydroxyl group is combined with an activating mechanism to activate the molecule by oxidizing the hydroxyl group with an oxidizing agent and a catalyst. Activating the molecule increases the binding affinity of the molecule.

In one embodiment, the molecule comprises a polyphenol. In an alternative embodiment, the molecule comprises a polymeric carbohydrate molecule or polysaccharide derivatives. In another embodiment, the polyphenol is derived from a plant. In an embodiment, the plant comprises *camellia sinensis*, or *punica granatum* or other polyphenol bearing plants. In another embodiment, the polyphenol is derived from the root, leaves, stems, bark, fruit or other tissues of polyphenol bearing plants.

In an alternative embodiment, the molecule comprises tannin, lignin, flavonoid, hydroxycoumarin, or alkaloids. In another embodiment, the molecule comprises at least an artificial synthetic section. In an embodiment, the catalyst comprises a catalase, a peroxidase, a phenoloxidases, a tyrosinase, or a metal catalyst. In an alternative embodiment, the catalyst is located at an animal cell. In another embodiment, the catalyst is generated by a pathogen. In an embodiment, the pathogen comprises virus, bacteria, fungi, an eukaryotic organism, or prionic. In an alternative embodiment, the oxidizing agent comprises reactive oxygen species (ROS).

In another embodiment, the reactive oxygen species comprises hydrogen peroxide. In another embodiment, the reactive oxygen species comprises inorganic or organic peroxides. In an embodiment, the reactive oxygen species comprises a product of ozone reduction by superoxide dismutase, glucose oxidase, hydration of a percarbonate, or hydration of carbamide peroxide (urea peroxide) or other indirect method of generating stable reactive oxygen species. In an alternative embodiment, the processed fluid is prepared from a dry mixture containing a polyphenol or a polysaccharide derivative. In another embodiment, the processed fluid is prepared from intact plant material containing a polyphenol. In another embodiment, the activating mechanism is initiated when the polyphenol or the polysaccharide derivative is in contact with the enzyme and the oxidizing agent in a solution. In an embodiment, the hydroxyl group becomes a carbonyl group after the activation of the hydroxyl group. In an alternative embodiment, the molecule comprises a quinonic group after the activation of the hydroxyl group. In another embodiment, the molecule has an effect in inactivating a pathogen after the activation of the hydroxyl group. In an embodiment, the oxidizing agent provides free radicals. In alternative embodiments, the activated molecule provides free radicals.

In a second aspect, a method of preparing a composition comprises obtaining a biopolymer from a plant and activating a hydroxyl group on the biopolymer, so that a molecular binding affinity of the biopolymer is increased.

In an embodiment, the biopolymer comprises a polyphenol, a polysaccharide derivative, or a polymeric molecule. In alternative embodiments, the activating is performed by placing the biopolymer in contact with an enzyme or an oxidizing agent. In another embodiment, the method further comprises cross-linking the activated biopolymer with a protein of an animal. In an embodiment, the method further comprises a plurality of biopolymers forming cross-linking structures among themselves. In an alternative embodiment, the method further comprises binding the biopolymer with a pathogen. In an alternative embodiment, the method comprises binding the biopolymer with a cell. In another embodiment, the method comprises binding the biopolymer with a virus. In a further embodiment, the binding of the polymer to multiple pathogens causes agglomeration or removal of microorganisms, proteins or proteinaceous structures from solution. In another embodiment, the binding ceases the propagation of the pathogen. In some embodiments, the activated biopolymer is capable of blocking a metabolic pathway of a pathogen. In an alternative embodiment, the method further comprises treating a diarrhea symptom of an animal using the activated biopolymer. In a further embodiment, the method comprises treating any damaged tissue of an animal using the activated biopolymer. In another embodiment, the activating the hydroxyl group is triggered by an enzyme on a site of an animal. In an embodiment, the activating the hydroxyl group is achieved by exogenous addition of an enzyme. In an alternative embodiment, the method further comprises removing or inactivating an oxidoreductase or a reducing compound that reacts with an oxidizer. In another embodiment, the method further comprises forming a barrier by cross-linking the biopolymer with a protein of an animal, so an invasion of a pathogen is prevented. In a further embodiment, the method comprises cross-linking the biopolymer with a protein of an animal, so as to promote accelerated wound healing.

In a third aspect, a method of facilitating a localized reaction comprises localizing an added reactive oxygen species in a reactive proximity of a hydroxyl group on a biopolymer, activating the hydroxyl group of the biopolymer, and applying the biopolymer to a target site.

In an embodiment, the biopolymer comprises a polyphenol or a polysaccharide derivative. In an alternative embodiment, the activating is achieved by causing an encountering of an enzyme. In another embodiment, the reactive oxygen species comprises hydrogen peroxide. In an embodiment, the method further comprises increasing the density of the hydrogen peroxide in the reactive proximity of a hydroxyl group by adding hydrogen peroxide to a solution containing the biopolymer. In an alternative embodiment, the biopolymer comprises multiple hydroxyl groups.

In a fourth aspect, a controlled chemical delivery method comprises preparing a bio-molecule containing a pre-selected chemical substance and selecting a size, a weight, or a combination thereof to control a penetration rate of the bio-molecule through an animal tissue.

In an embodiment, the chemical substance comprises a phenolic compound. In an alternative embodiment, the chemical substance comprises quinonic compound. In another embodiment, the bio-molecule comprises some amount of an extract from a plant. In an embodiment, preparing the molecule comprises isolating the molecule. In an alternative embodiment, selecting comprises extracting. In another embodiment, the penetration rate is moderate, so that an application of the bio-molecule to an animal does not cause a toxic response from the tissue of the animal. In a further embodiment, an application of the bio-molecule to an animal reduces the external stimulation of immune response from the animal system. In an embodiment, the ingestion of the bio-molecule improves the utilization of nutrition for growth in animal systems.

BRIEF DESCRIPTION OF THE DRAWINGS

FIG. 1 illustrates several reaction pathways for phenol unit conversion into quinones in accordance with an embodiment of the present application.

FIG. 2 illustrates a composition prepared in accordance with one embodiment of the present application.

FIG. 3 illustrates a flowchart of a method of preparing a plant-based composition in accordance with one embodiment of the present application.

FIG. 4 illustrates a flowchart of a method of inactivating reducing agents/enzymes using a solvent in accordance with one embodiment of the present application.

DETAILED DESCRIPTION OF THE INVENTION

Figure 1:
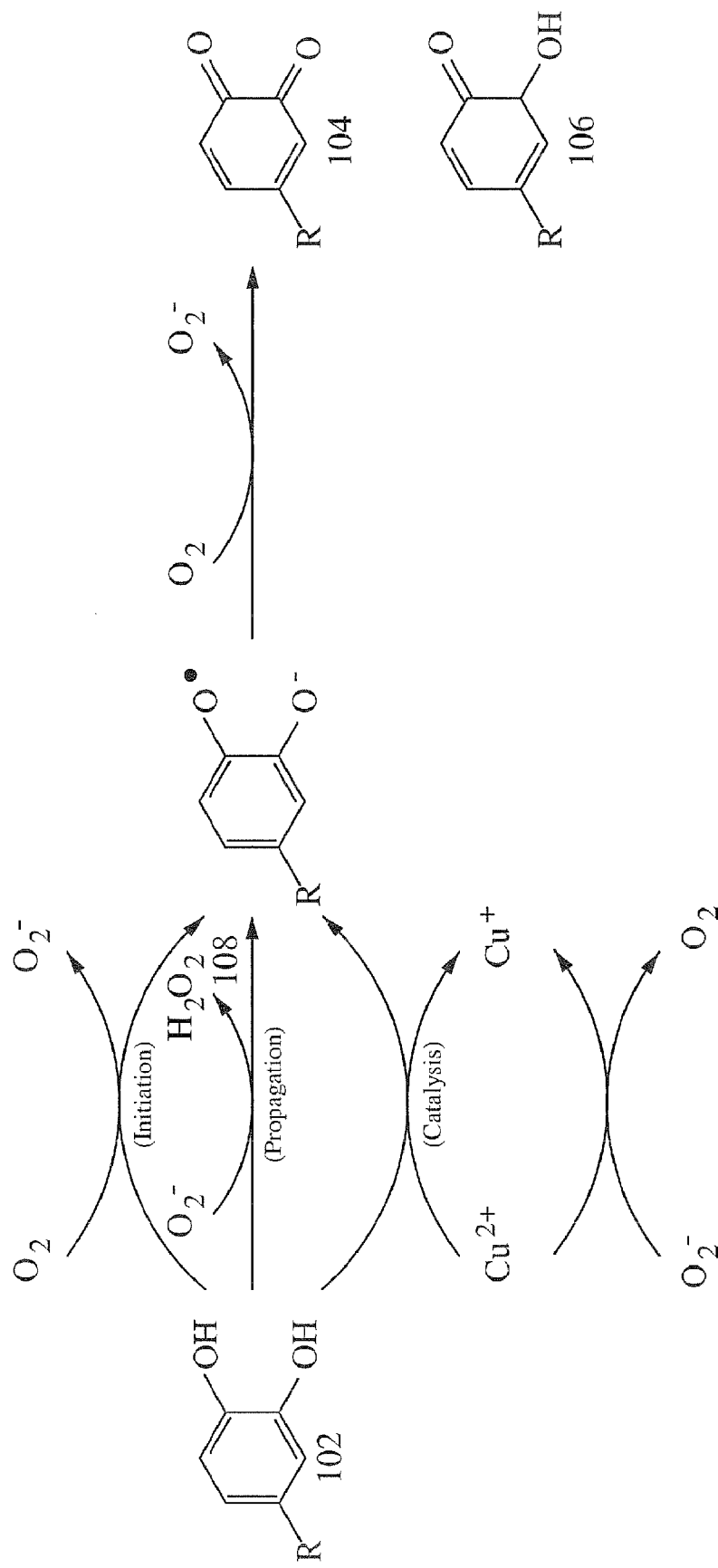

The present invention comprises novel bioactive compositions. In an aspect, a biochemical system comprises a biopolymer or the synthetic equivalent combined with a stable source of reactive oxygen species (ROS) and a separate source of an oxido-reducing enzyme or catalyst. The combinations of the substances are able to cause the formation of an oxidized biopolymer with increased protein binding affinity and microbial control activity.

Some embodiments of present invention contain a mixture of plant based material with astringent and/or germicidal properties and an activation precursor in stable solution. The solution is substantially free of enzymes and catalytic substances that can cause the other components to react in a manner that causes degradation. The mixture of this plant based germicidal material and activation precursor is catalyzed by various enzymes of animal, plant or microbial cells to release oxidative radicals and to form an activated plant based material with significantly enhanced astringent and germicidal properties. The release of oxidative radicals and the formation of activated plant material are generally localized to the catalyzing biologic enzyme source, thus concentrating such activity in the proximity of the triggering biologic entity or material for maximum effect. The triggering catalyst can also be of non-biologic origins such as a metal that causes reduction of the activation precursor to cause auto-oxidation of the plant based material into its activated form.

In alternative embodiments, the bioactive and germicidal system contains a mixture of a plant based material, such as polyphenols. A person of ordinary skill in the art would appreciate that any macromolecules, polymers, aggregate of small molecules, cellular membrane fragments, cross linked compounds containing a multiplicity of exposed phenolic units and an activation precursor (e.g., an oxidizer, such as hydrogen peroxide), or combinations thereof are applicable.

In other embodiments, activator materials contain ozone or peroxone. In some embodiments, the plant material can be a source of naturally occurring hydrogen peroxide.

However, an endogenous concentration of $H_2O_2$ is highly variable and can generally be lost in the processing of the plant material. One of the advantageous aspects of some embodiments is that the source of the oxidizing agent can come from exogenously added hydrogen peroxide, ozone, peroxone or other commercial oxidizer as the activation precursor.

In some embodiments, a phenol unit can carry 1 to 3 hydroxyl groups (OH) that can react with the oxidizer. Therefore, a phenolic groups contained macromolecule composed substantially of can carry hundreds to thousands or more hydroxy groups. This high density molecular cluster of hydroxy groups provides various other non-covalent-bond opportunities, charge attraction, and physical sequestration for hydrogen peroxide molecules within close and reactive proximity to the phenolic units. Sequestration in accordance with embodiments of the present invention provides a novel method of maintaining stability and enhanced saturation of hydrogen peroxide within the reactive proximity of the polyphenolic substrate at lower concentration solutions than the equivalent non-sequestered components. Sequestration can be the result of combining a sufficiently high concentration of hydrogen peroxide in water to establish intermolecular attractive forces between a substantial portion of the polyphenol hydroxyl functional groups and the hydrogen peroxide molecules. Increasing sequestration can significantly reduce oxidizer loss from heating, ultraviolet exposure, reducing contaminants, and spontaneous degradation while increasing the potential number of high affinity binding sites on the polymer upon encountering the appropriate enzymes.

In some embodiments, some amount of crude extracts of plant material, including the fragments of plant cells populated with partially denatured reactive oxygen species (ROS) processing enzymes like catalase, peroxidase, dismutase, glucose oxidase, or a combination thereof, can function as a hydrogen peroxide sequestration structure. These ROS include hydrogen peroxide ($H_2O_2$), superoxide ($O_2^-$), singlet oxygen ($^1O_2^*$), and hydroxyl radical (.OH). In alternative embodiments, the activation precursor can be generated by the degradation of dissolved ozone ($O_3$) or by its conversion by active dismutases into $H_2O_2$. In other embodiments, the activation precursor can also be generated by the enzymatic conversion of any superoxide, such as a fatty acid peroxide.

The component of the composition that contributes the phenol units can contain a polyphenol and/or any heterogeneous or homogenous macromolecule that is synthetic, plant, or animal derived. In some embodiments, the polyphenol contains more than two phenol groups. In alternative embodiments, the polyphenol contains more than 30 phenol groups. In other embodiments, the polyphenol contains from 100 to 10,000 phenol groups. A person of ordinary skill in the art would appreciate that any number of phenol groups can be contained in the composition so long as the compositions contain the desired features described herein, such as the rate of absorption is moderate.

Plant based materials described herein include, but not limited to, polyphenols, lignins, polysaccharides and other large molecule materials or structures that are predominantly terminated by carbonyl groups that are available for quinone transformation. Effective solutions can be processed from a vast variety of different plant tissues of different species due the ubiquitous nature of appropriate materials.

The typical art for obtaining antimicrobial compounds from botanical sources relies on mechanical or solvent extraction of organic molecules in manners that do not provide practical means for harnessing the wound response chemistry of living plant tissues for commercial application, especially in animal or other plant systems. Cellular disruption, whether from commercial processing, pathogen attack, herbivores, environmental damage or natural decomposition, triggers the reactions and makes the antimicrobial compounds useless in a very short period of time.

Polyphenols constitute a vast range of organic polymers produced by plants and are important substrates in the wound response of plants. These polymers are able to undergo some oxidative conversion to form antimicrobial compounds, but may produce slightly different behaviors. Polysaccharides may also undergo some oxidative transformation, forming bioadhesives with antimicrobial and wound sealing potential and can be effective quinone analogues.

The underlying processes are rooted in a complex series of chemical reactions that may involve multiple direct and indirect enzymatic formations of highly reactive intermediates. oxidoreductases can mediate this chemical cascade, typically in the presence of a source of reactive oxygen species, with several possible modalities converting hydroxyl (OH) functional groups of aromatic polymers into carbonyl groups (═O) that form covalent bonds responsible for high strength biologic structures and antimicrobial defenses. Carbonyl groups are functional groups contain a carbon atom double-bonded to an oxygen atom: C═O. Ketone groups contain carbonyl groups (C—C(═O)—C) that each of the carbonyl groups bonds to two other carbon atoms with the carbon atom of the carbonyl. Some of the particular interested substrates include compounds with multiple aromatic subunits forming organic molecules with fully conjugated cyclic dione structures with >C(═O) groups in any arrangement of double bonds, including polycyclic and heterocyclic analogues, that form covalent bonds to nucleophilic amino acids and proteins. The term "quinonic" used in this document includes any compounds containing subunits with any number of carbonyl groups.

The converted or oxidized hydroxyl subunits exhibit increased binding affinity characteristic of multiple quinones and semiquinones in a heteropolymer or homopolymer configuration. The oxidation is able to only take place on a portion of the functional groups of a polyphenol. The typical heterogeneous character of these oxidized polyphenols is able to present quinonic activity while retaining some basic polyphenol behavior. Differences in gross structure, tertiary form, and molecular weight will cause different affinities for different proteins with increased gross mixture or intramolecular heterogenicity providing broader spectrum potential.

Besides having been identified as a transient cofactor in a number of biologic cross-linking activities, quinone monomers have long been known for a very potent germicidal effect.

In addition to provide a source of stable free radicals, quinones are able to irreversibly complex with nucleophilic amino acids in proteins, often leading to inactivation of the protein and loss of associated biologic function. For that reason, the potential antimicrobial effect of quinonic compounds is great. Probable targets in the microbial cell are surface-exposed adhesions, cell wall polypeptides, motility effectors and membrane-bound enzymes. Quinones can also render substrates unavailable to the microorganism.

As with all plant-derived antimicrobials, the possible toxic effects of quinones must be thoroughly examined. Some quinones have demonstrated antimicrobial effectiveness at 5 to 6 log dilution. Quinone monomers are small molecules that easily penetrate tissues and exhibit toxicity that can limit their medicinal use, whereas polyquinonic compounds contain a multitude of quinonic segments in a biopolymer, compound molecule, or synthetic analog. Polyquinonic compounds of sufficient molecular weight and size can have reduced systemic absorption, corresponding to reduced toxicity potential to higher organisms.

The study of germicidal activity of quinone compounds started as early as early 1900s but was not well understood until the 1940s. Formalin inhibition of the color reaction between quinone and many different proteins, such as egg albumin, casein, horse serum, and peptone, indicates that the reaction is principally between quinones and the amino group of proteins. The germicidal mechanism of a polyquinone alone can take three primary forms: the covalent binding reaction with bacterial proteins, cross-linking of ruptured cell cyto-proteins to astringently form a barrier refractory to pathogens, and a REDOX cycling mode that generates peroxides and free radicals that cause oxidative damage to the pathogen envelope.

The major product of phenol oxidation was identified by Pryor in 1940 as o-diphenols. This production can result from auto-oxidation in the presence of oxygen radicals or from enzyme conversion by phenoloxidases. Phenoloxidases (e.g., L-dopa: oxygen oxidoreductase; EC 1.14.18.1), also known as polyphenol oxidases and tyrosinases (e.g., lysyl oxidase; EC 1.4.3.13), are copper-containing proteins that catalyze the oxidation of monophenols into o-diphenols and the subsequent oxidation of o-diphenols to the corresponding o-quinones. Phenoloxidases are widespread in the animal kingdom, as well as in plants, fungi, and prokaryotes. Insects also use them in sclerotization in rapid formation of high strength egg casings, cocoons and silk structures.

Even though they are the result of hundreds of millions of years of divergent evolution, the very close structural similarity of oxidative enzymes including peroxidase, polyphenol oxidase, laccase, etc., found in plant, fungi, bacteria and peroxidases such as myeloperoxidase, lactoperoxidase and all the peroxidases from different animal tissues, indicates the need to achieve the same basic biologic ends. This functional similarity can be utilized as a novel method for triggering controlled oxidation of polyphenols across biologic kingdoms or phyla.

For example, tyrosinase is the core enzyme of the phenoloxidase family along with several other oxidoreductases that catalyze a step in the formation of melanin pigments. The tyrosinase in mammals is functionally similar to phenoloxidase in the chemical cascade that causes sclerotization, melanization, and production of antimicrobial peptides in insects.

Hydrogen peroxide is one of the most common biologic sources of reactive oxygen species involved in the enzymatic creation of polyquinones. It is expressed in substantial quantity in live tissues of many plants. It is a ubiquitous metabolic product and a key initiator that is consumed in the polyphenol oxidation process that occurs in damaged tissues. Both the oxidizer ($H_2O_2$) itself and its enzyme mediated reaction product, polyquinones, are antimicrobial with the latter also having strong astringent properties. These are the primary compounds that enable the traditional medicinal use of many fresh plant materials as wound dressings. However, antimicrobial potential within the vicinity of a fresh cut plant tissue is largely degraded within minutes due to the transient nature of these compounds in wounded plant tissue.

The mixture of plant materials, oxidizers and enzymes have been used to generate oxidized polyphenols and carbohydrates for a variety of industrial and commercial uses, but the composition of plant material with enzymes denatured or removed to allow stable combination with oxidizer for the purpose of applying to a target that provides a separate source of catalyst or enzyme to affect biologic systems is novel.

References describing compositions of plant materials and oxidizers for use on biologic systems is limited. U.S. 2002/0034553 describes an aloe vera gel and Irish moss as a thickened passive carrier for delivering hydrogen or zinc peroxide as a source of oxygenation to create unfavorable conditions for anaerobic bacteria on dermal wounds. U.S. Pat. No. 5,260,021 discloses a hydrogen peroxide-containing gel ointment as a vehicle for carrying oxygen for use only as a disinfectant for contact lenses or the like. U.S. Pat. No. 4,696,757 describes a hydrogen peroxide carrying gel for treating surface cuts and for bleaching hair. None of these patents make reference to combining an oxidizer, such as hydrogen peroxide, and a polyphenol component with the intent of causing or enabling a reaction between the two.

In higher plant physiology, hydrogen peroxide, polyphenols, proteins and oxidoreductases are segregated in the structured cytoplasm, organelles and membrane structures of the living cell. Disruption of the cell by infection, injury, crushing, pulverizing, desiccating, ensiling or other physically damaging processes result in the mixing and exhausting of the useful reactive potential of these components. The current art of botanical extraction offers no obvious means to capture a stable combination of these components. It is therefore not surprising that despite over 50 years since the discovery and documentation of the function of oxidized polyphenol systems within plants, the botanical health and agriculture industries have not successfully commercialized this multi-molecular chemistry, instead focusing on capture of inherently stable nutritional and pharmacologic molecules that can be simply packaged or extracted.

There is significant understanding of enzymatically oxidized polyphenols within the botanical sciences, but there is no known reference for a stable ex-vivo method and composition for restoring, duplicating, or enhancing the capability of this polyphenol oxidation system for use with animal physiology or other biologic applications outside the context of in-vivo plant biochemistry.

The environmental interfaces and immunologic needs of the plant kingdom are in many ways similar to those of animals. External plant tissues, such as leaf cuticles, fruit rinds, and seed husks, are living tissues adapted to defend against similar pathogens and physical stresses as human derma and mucosa. Animals and plants also have some analogous mechanisms for coping with wounding. As such, the biochemical mechanisms used in the plants are able to be applied to animals.

In another aspect, a method of producing stable biochemical systems comprises extracting a stable polyphenol substrate in a composition free of active reducing agents, enzymes or catalysts and combining the polyphenol substrate with a concentrated source of reactive oxygen species that promote initiation and propagation of oxidation reactions when applied to or combined with a separate source of appropriate oxidoreductases or catalysts.

Compositions in accordance with some embodiments of the invention introduce hydrogen peroxide in sufficiently high concentrations into an aqueous plant biopolymer solution to establish sequestering or stabilizing of concentrated oxidizers within intimate reactive proximity of the hydroxy functional groups of the polyphenols. The sequestered oxidizer resists diffusion away from the biopolymer when subjected to dilution. Reducing agents are removed or denatured in formulations containing the oxidizer-polyphenol combination to render the oxidizer-polyphenol combination substantially unreactive to proteins until brought in contact with a surface, tissue, organism, coating or solution that provides a source of oxidoreductase enzymes or other catalytic agents that directly or indirectly mediate conversion of the biopolymer into an activated form.

In another aspect, the compositions contain an efficient target-specific formation of oxidized biopolymers mediated by enzymes of animal origin. This mechanism enables the delivery of medically and commercially useful effects to animal body tracts or tissues. These effects are analogous to basic plant wound responses. Many of the biochemical reactions involved are well studied but still not fully understood. Nonetheless, there is no prior art for stabilizing and applying the stabilized combination of oxidizers and polyphenols to animal physiology or pathogens as the source of enzymatic activation. Common phenol complexing acting enzymes in many plants, bacteria, and fungi such as laccases or phenol oxidases are functionally similar to common animal enzymes, such as catalases, peroxidases, that can also cause the formation of quinonic groups with enhanced affinity for amino acids of proteins.

In some embodiments, the liquid solution prepared has many significant practical advantages over conventional typical antimicrobial botanical extracts. These include increased water solubility and deliverability, broader pH stability, higher temperature stability, predictable potency, low animal toxicity, low minimum inhibitory concentrations on a broad spectrum of gram negative and gram positive bacteria, low odor and taste, efficiency in use of raw materials, and lack of harmful environmental breakdown products.

Some embodiments of the present invention mimic plant defense mechanisms that have co-evolved with environmental pathogens over many millions of years. The non-specific protein binding action of the activated biopolymers contain multiple activities that can cause microbial inactivation. All are radically different than conventional germicidal or antibiotic actions and are far less likely to promote resistance in a manner that has been associated with subtherapeutic use of and environmental contamination with, antibiotics.

The oxidized polyphenols can have several biologic mechanisms of action. A single such polyquinonic molecule can contain several to thousands of binding sites in a dense and non-diluting population, so that the compound can cross-link and condense amino acids and proteins of damaged organisms to form a refractory barrier against pathogens and irritants. The compound is able to bind to and cause significant distortion and inactivation of the metabolic pathways and virulence effects of the pathogens. They are able to physically agglomerate, entrain or immobilize pathogens to prevent the pathogens from propagating. Quinonic or phenolic forms also can cause oxidative radical release to cause pathogen membrane damage and lysis. They are also able to block receptors responsible for pain and inflammatory responses.

Polyphenols generated in accordance with embodiments of the invention can be individual soluble polymers, compound molecules, macromolecular conglomerates, or aggregates with proteins or cellular fragments. Stabilizing sequestration of the oxidizers can result from hydrogen affinities, electron sharing, or from capillary effects on a larger scale.

In many situations, it can be beneficial to promote heterogeneous mixtures of activated biopolymers to maximize bioactivity/bioavailability against a broader range of pathogens. The combination of polyphenols extracted from multiple plant materials can serve to further broaden the binding spectrum. In some cases, not all phenol subunits undergo quinone conversion and the substrate can retain characteristics and behaviors of the unoxidized compounds in addition to the quinonic behavior.

Those of ordinary skill in the art will understand that many other natural or synthesized organic polymers can also be oxidized to form a multiplicity of carbonyl or quinonic functional groups that can be used in place of or combined with polyphenols.

In some aspects, non-botanical enzymes are used to trigger the oxidation of polyphenols. This allows introduction of a stable polyphenol-oxidizer solution to passively traverse animal body tracts to deliver unreacted materials to compromised tissues that cannot be practically accessed by other means, thereby increasing the effective bioavailability of the useful composition. Target catalyzed quinone formation constrains the non-specific biochemical reactions to the immediate proximity of compromised tissue, thereby reducing the risk of undesirable effects of gross tissue or systemic interaction.

The existence of functionally identical enzymes in the animal and plant kingdoms enable the novel transference of the enzyme mediated polyphenol reactions to non-botanical applications. For example, the G.I. tract of higher vertebrates has 2 different types of peroxidases. The first type comprises a soluble peroxidase found in both rat and pig digestive mucus that is secreted from the immune system eosinophil. The second type comprises an insoluble peroxidase found in G. I. mucosal cells that are only released in wounding. The second type of peroxidase is basically the functional equivalent to peroxidases involved in polyquinone formation of plant wound response and can site-specifically trigger quinonic activity in the direct proximity of damaged, vulnerable, or infected cells while remaining passive to healthy tissue.

Such a stable polyphenol-oxidizer composition has particularly useful biochemical effects on a tissue lesion or an irritated mucus membrane of the digestive tract, respiratory tract, urinary tract, reproductive tract, or other mucosal interfaces within higher animals. Ingestion of the composition in liquid solution will passively deliver it to the site of damaged cells and infection where oxidoreductase enzymes will catalyze polyquinonic activity. The polyquinones will cross-link and condense cellular proteins of damaged host cells into a protective barrier. The non-specific high-affinity binding to surface proteins, enzymes, receptors, and structures critical to metabolism, virulence, and motility immobilize and inactivate a very broad spectrum of pathogens. The agglomeration of pathogens can also increase the potential antigenicity to evoke host immune responses.

In an aspect of the present invention, the strong but localized astringent effect on the affected tissue can also reduce fluid exudates. Non-localized gross astringency from high concentrations of tannins and other polyphenols in the digestive system are known to interfere with nutritional absorptions and can cause mucosal damages; whereas, target-localized activation of quinonic behavior minimizes these concerns.

In some aspects, the compositions comprise novel bioactive microbial control and tissue protective systems. The mixture of the bioactive material and activation precursors are catalyzed by various enzymes of animal, plant, or microbial cells. If the activating enzyme is associated with tissue of interest such as wounded or infected tissue, the ingestion or application of the not activated composition will allow passage to compromised tissue even deep in a body tract. Release of oxidative radicals and formation of activated plant material site-specifically on target tissue significantly increases bioavailability and constrains the enhanced activity to the immediate proximity of the enzyme source for reduced collateral interaction with other tissues.

In some of the embodiments, the bioactive plant-based material can be polyphenols or any bio-molecules, synthetic polymers, aggregates of small molecules, cellular fragments, or cross-linked groups of compounds comprising a multiplicity to tens of thousands of exposed reacting sites Many plants can be used as an inexpensive source of appropriate polyphenols. *Camilla Sinensis* leaf is an example that can be a good source of a botanical raw material because of common availability of cultivated sources, documented low natural toxicity and high water soluble polyphenol content. The flavonol group of polyphenols (non-oxidized catechins) constitutes up to 30% of the dry leaf weight of *camellia sinensis*, making it an economical source. Effective antimicrobial astringent compositions have also been produced from many different plant species and structures including rye seeds, mung beans, daikon skin, pomegranate rinds, bearberries, aloe vera skin, organ pipe cactus, Chinese gall, oregano leaves, persimmon fruit, wheat germ, barley seeds, and coffee beans, demonstrating the ubiquitous nature of this plant defense mechanism in the plant kingdom.

In some aspects, methods of extracting a polyphenol substrate from plant materials enable stable formulation, storage, and delivery by having extracts that contain substantially free active oxidoreductases or other reducing agents. Some aspects of the invention involve thermal or solvent denaturing of plant raw materials to obtain plant biopolymer component free of active polyphenol oxidizing enzymes. Raw material supply availability and different plant tissue types can possibly dictate different processing. For instance, desiccated or dried plant materials are already devoid of hydrogen peroxide and therefore can undergo enzymatic denaturing processes after polyphenol extraction.

An example of an efficient process for producing an economical polyphenol raw material source free of degrading enzymes comprises desiccating freshly harvested whole *camellia sinensis* leaves rapidly in high temperature air to denature the polyphenol oxidases that can cause oxidation of green leaf polyphenols. This process maintains a very close composition to live tea leaves with the exception of the loss of hydrogen peroxide, water, and a few enzymatic changes that typically occur extremely rapidly upon harvest. The leaves are then pulverized to facilitate handling and extraction efficiency.

In contrast, black tea undergoes an example of an alternative manufacturing process. In the manufacturing process, *Camilla sinensis* leaves are crushed and their cellular structures are disrupted while still containing active polyphenol oxidase. This initiates enzymatic aerobic oxidation of catechins into quinones that spontaneously condense to form volatile compounds. Plant material so processed is still able to be a useful source of polyphenols, but the plant material will have lower content of polyphenols and will require additional enzyme denaturing by heating the plant material or its extract to a temperature sufficient (preferably 80° C. to 110° C.) to blanch or denature the enzymes. A protein denaturing solvent, such as ethanol, is able to be alternately used in the plant material extraction process to destroy or remove cellular enzymes.

Most plants produce hydrogen peroxide as part of routine biologic activities as well as in response to stress. The concentration of $H_2O_2$ in plant tissue varies tremendously by species, tissue type, environmental stress and seasons. It is lost or consumed in typical post harvest processing and is generally impractical to capture from natural sources, especially given the low cost of synthetic equivalent oxidizers.

In some embodiments, the methods and compositions in accordance with some embodiments of the present invention comprise the exogenous addition of hydrogen peroxide, which can be a commercially practical and stable source of reactive oxygen species for improved generation of quinonic subunits within the polyphenols. A person of ordinary skill in the art will also understand that other direct sources of reactive oxygen species can be used for various applications, such as ozone, zinc peroxide, peroxidases, carbamide peroxide, sodium percarbonate, calcium peroxide, magnesium peroxide, sodium perborate monohydrate, ozonide ($O_3^-$), superoxide ($O_2^-$), oxide ($O^{2-}$), dioxygenyl ($O_2^+$) or indirect source(s) of reactive oxygen species, such as oxygen gas, disassociated water, catalytic decomposed fatty acids, glucose, and polyphenols are able to be used.

In some aspects, embodiments of the present invention include combinations of high concentration reactive oxygen species, such as hydrogen peroxide, with a polyphenol substrate to provide a stabilizing environment that resists diffusion of hydrogen peroxide molecules away from intimate reactive proximity to the phenol subunits. Polyphenol structures provide many non-covalent bond opportunities and charge attraction to hydrogen peroxide molecules. Hydrogen peroxide is also a product of the auto-oxidation of polyphenols, helping to maintain gross equilibrium in solution. Stable sequestrations are able to shield the hydrogen peroxide from heat, ultraviolet exposure, reducing contaminants, and spontaneous degradation.

FIG. 1 illustrates several reaction pathways for phenol unit 102 conversion into quinones 104 or semi-quinones 106 in accordance with one embodiments of the invention. As used herein "quinone" refers to all quinonic compounds, such as quinones and semi-quinones. Hydrogen peroxide 108 can be both a source of reactive oxygen species for initiating oxidation, and can also be a product of polyphenol oxidation. Stable equilibrium in a solution with polyphenols can therefore be established. Once started, the source of reactive oxygen species (ROS) facilitates efficient propagation of quinone generation through polyphenol substrates even without direct enzymatic mediation. Concentrated $H_2O_2$ in water is therefore a good oxidizer component. However, hydrogen peroxide can be indirectly achieved through other reactions, such as decomposition of ozone, fatty acids, or percarbonates to name only a few such reactions. Cellular oxidoreductases can also be involved in the indirect generation of the oxygen species involved in the initiation or propagation of the oxidation reaction cascade. For example, the catalase that defends animal cells and many pathogens from ROS damage will disassociate $H_2O_2$ into water and reactive oxygen species.

Hydrogen peroxide is naturally produced in plant and animal cells but its concentration can vary tremendously depending on species, season, stress, and tissue type. Although certain plant types, such as succulents, can store significant quantities of hydrogen peroxide in their tissues, it is generally impractical to extract it from plant sources due to the presence of reducing enzymes segregated from the hydrogen peroxide and/or polyphenols only by delicate subcellular divisions that are inevitably breached by typical commercial extraction processes. Mixing triggers the oxidative wound response and rapidly consumes the hydrogen peroxide, leaving excess polyphenols, enzymes, and other non-involved botanical compounds.

Some aspects of the present application include the use of a separately manufactured or generated source of reactive oxygen species in combination with the polyphenol substrate substantially free of active reducing agents or enzymes.

In some embodiments, the oxidizer-biopolymer compositions are aqueous solutions. In alternative embodiments, fibers, hydrogels, microporous media, micelles, emulsions, and other structures physically encapsulate the biopolymer-oxidizer composition. In still other embodiments, mixtures of dry powders, granules, or other non-liquid polyphenol bearing materials combined with a dry oxidizer, such as potassium percarbonate, are used as a kit to be hydrated to produce a useful polyphenol-oxidizer solution.

In some embodiments, the catalyst is delivered to the target site separately as a liquid, aerosol, or as a surface coating on an applicator, dressing, or cleaning implement. An example of this is an absorbent sponge infused with a reducing agent, such as catalase or copper, that will cause rapid release of oxygen radicals and quinone formation when brought in contact with a polyphenol-oxidizer composition. This can be used to generate a strong germicidal action, particularly to destroy viruses on non-biologic surfaces or to sanitize healthy tissues in the absence of exposed catalyzing enzymes. For example, viral envelopes generally do not have enzymes, but are made up of proteins that can be bound by polyquinones. Thus, a separately delivered catalyst or enzyme can be used to initiate the viral/germicidal reactions.

In some aspects, polyquinonic compounds in accordance with the embodiments comprise utilities such as a microbial flocculant. Adding these polyquinonic compounds to a contaminated water source can cause aggregation of the microorganisms into masses that either precipitate out or can be more easily filtered out by mechanical means. The deposition of polyquinonic compounds on mechanical filter media can trap proteins and microorganisms while imparting germicidal characteristics. This can be accomplished by applying an activated polyquinone to a filter media or circulating polyquinone forming compositions through a filter media that has a catalytic aspect to its surface such as a bacterial biofilm. This can find application in many recirculating and single-pass filtration applications.

Figure 2:
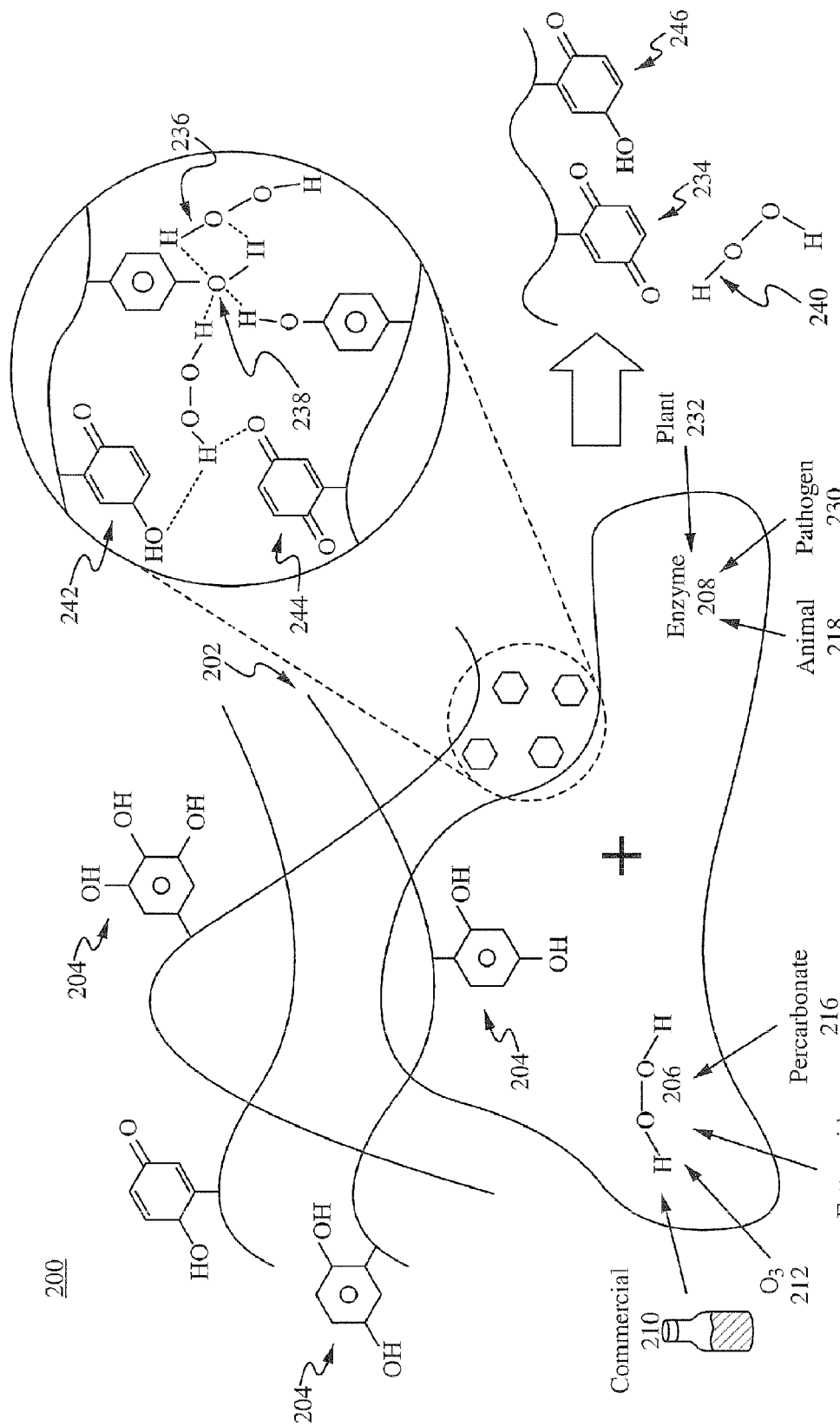

FIG. 2 illustrates a composition 200 prepared in accordance with some embodiments of the present invention. The composition 200 contains biopolymers 202 containing hydroxyl group contained molecules 204. The hydroxyl group contained molecules 204 are illustrated as polyphenols, but can be phenols, polyphenols, polysaccharides, or combinations thereof. In alternative embodiments, the hydroxyl group containing molecules 204 are tannins, lignins, and flavonoids. A person of ordinary skill in the art would appreciate that the biopolymers 202 are able to be any short linkage molecules (such as 2 to 100 repeating units or 100 to1000 repeating units), macromolecules, long chain molecules, ring structured molecules, π electron stacking and/or structural stacking molecules. Further, the biopolymers 202 are also able to be any substance that can be derived or obtained from plants or artificial synthetic molecules. Moreover, the biopolymers 202 are able to be obtained from combinations of plants. For example, the extract of plant A contains a high ratio of polyphenols and the extract of plant B contains a high ratio of polysaccharides. The biopolymer 202 can be obtained from a mixture of the extracts of both plant A and plant B. In such a case, 70% of the biopolymer 202 can come from plant A and 30% of the biopolymer 202 can come from plant B, so that the composition 200 can have chemical properties closer to polyphenol than to the chemical properties of polysaccharides. Thus, desired reactive properties of the composition 200, such as a desired reactivity and reaction rate, can be designed by using different combinations of the plants A and B.

The composition 200 is also able to contain an oxidizing reagent 206 and/or an enzyme 208. In some embodiments, the oxidizing agent 206 comprises reactive oxygen species. In some embodiments, the oxidizing agent 206 comes from commercially available hydrogen peroxide 210, such as >60%, 20%-60%, 35%, and 8%-20% of $H_2O_2$ in water. In alternative embodiments, the oxidizing agent 206 comprises 1-2% or less than 10% $H_2O_2$ in water. In some embodiments, the oxidizing agent 206 comes from a reaction of ozone 212, fatty acid 214, or percarbonate 216. In some embodiments, the oxidizing agent 206, such as hydrogen peroxide, is endogenously produced by the biopolymer or the plants. In alternative embodiments, the oxidizing agent 206 is exogenously added to the system, such as by adding commercially available hydrogen peroxide to a solution of the biopolymer 202 and the enzyme 208.

In some embodiments, the enzyme 208 is endogenously generated or exogenously added. For example, the enzyme 208 used to activate or facilitate the reaction is generated by pathogens 230 on the tissue of an animal 218. Alternatively, the enzyme 218 is generated at the cells/tissues of animals 218 and/or plants 232. Moreover, the enzyme can be added to a solution containing the biopolymer 202 and the oxidizing agent 206 before applying the composition 200 to an animal or a plant.

In some embodiments, the hydroxy group contained molecule 204 forms quinonic compounds 234 and/or 246. The quinonic compound 234, 242, 244, 246, hydroxy group 236, 238, 240, and the hydroxyl group contained molecule 204 can provide interactions, such as covalent bonding forces, hydrogen bond interactions, or electron stacking interactions, to keep the reactive oxygen species (ROS) localized in the reactive proximity. The reactive oxygen species can be oxidizing reagents.

Figure 3:
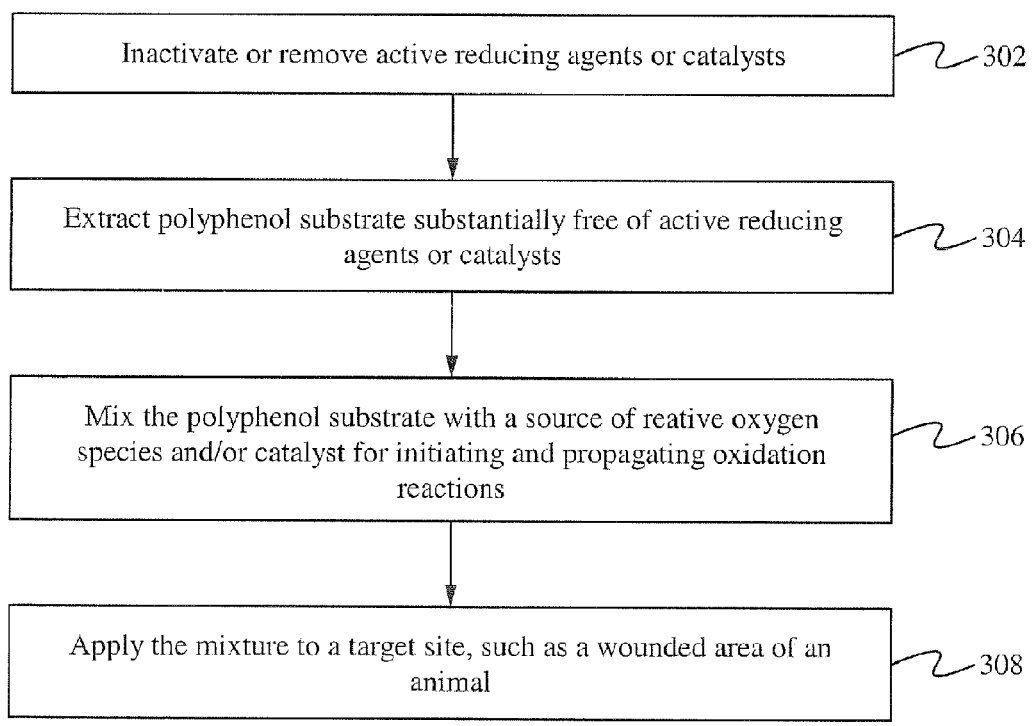

FIG. 3 shows the step 300 of a process for preparing a plant-based composition in accordance with one embodiment of the present invention. At Step 302, active reducing agents or catalysts are inactivated or removed. At Step 304, polyphenol substrates substantially free of active reducing agents or catalysts are extracted. At Step 306, the polyphenol substrates are mixed with a source of reactive oxygen species and/or catalysts for initiating and propagating of oxidation reactions. As described above, the source of reactive oxygen species, such as hydrogen peroxide, can be exogenously added or endogenously generated by a plant extract. Similarly, the catalysts for initiating the oxidation reactions can be exogenously added or endogenously generated at an applied site, such as a pathogen-infected site or a tissue wounded area. At Step 308, the mixture is applied to a target site, such as a wounded area of an animal. The method 300 described above is one embodiment. All the steps are optional, and additional steps are able to be added. The sequence of the steps can be in any order. Other variations are applicable. For example, a solution, substantially free of reducing catalysts and containing polyphenols extracted from a plant, is mixed with hydrogen peroxide. The solution is able to be stored in a container for a later activation process. The solution is activated through an activation mechanism after being delivered to a pathogen-infected site of an animal, which generate catalysts for activating the reactions. In other examples, a solution containing polyphenol and hydrogen peroxide is activated by exogenous addition of catalysts before the application to a target, such as a site of an animal or a plant.

Figure 4:
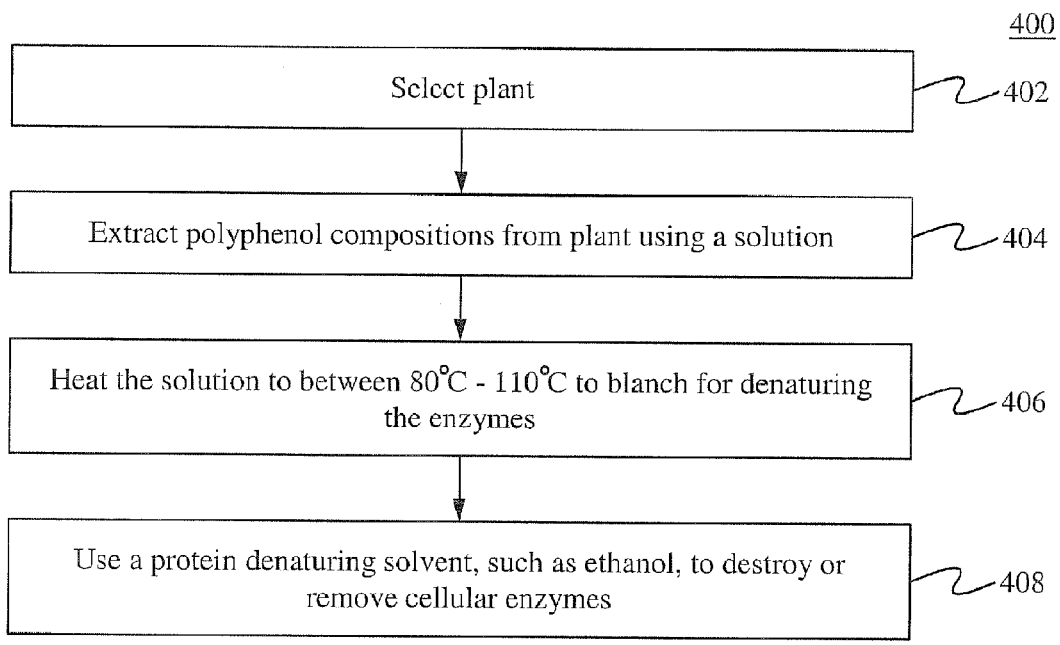

FIG. 4 shows the step 400 of a process for inactivating reducing agents/enzymes by solvent in accordance with an embodiment of the invention. At Step 402, the plants that are used to make the plant-based composition are chosen. At Step 404, polyphenol compositions are extracted from the plant using a solution. At Step 406, the solution is heated to between 80° C. to 110° C. to blanch for denaturing the enzymes. At Step 408, a protein denaturing solvent, such as ethanol, is used to destroy or remove cellular enzymes contained in the plant.

Figure 5:
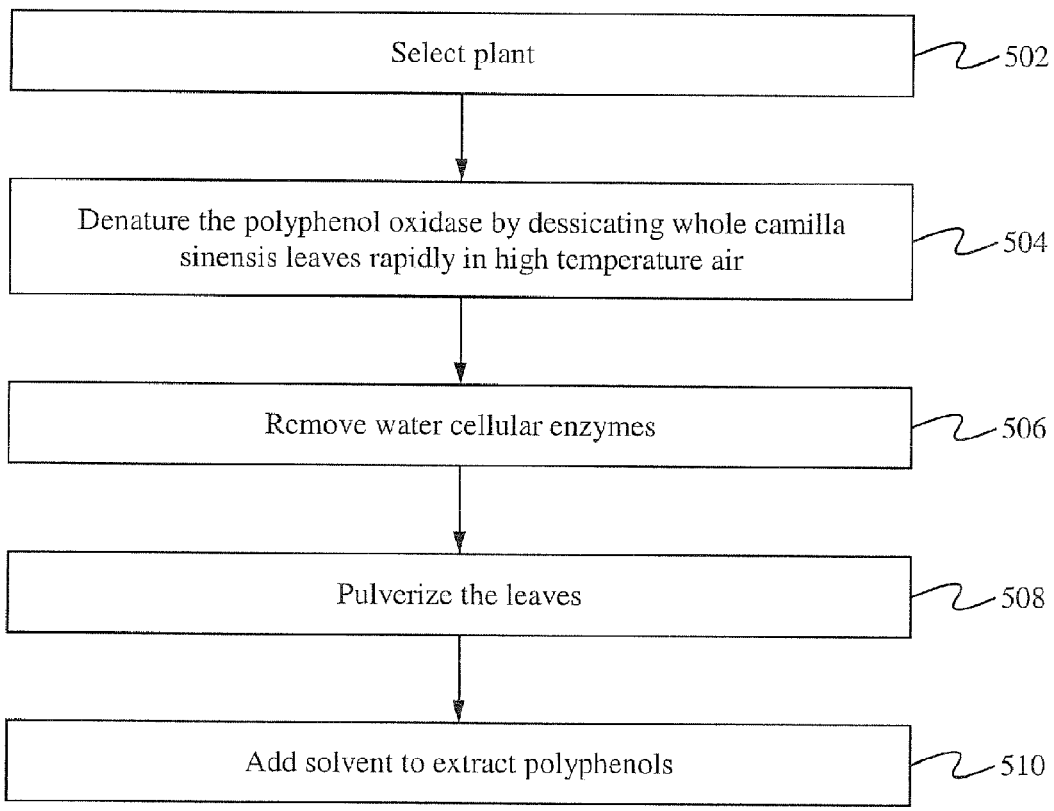
FIG. 5 illustrates a flowchart of a method of heat inactivating reducing agents/enzymes in accordance with one embodiment of the present application.

FIG. 5 shows the step 500 of a process for inactivating reducing agents/enzymes by heat in accordance with an embodiment of the invention. At Step 502, the plant used to make the plant-based composition is chosen. At Step 504, the polyphenol oxidase from the plant is denatured by desiccating whole *camellia sinensis* leaves rapidly in high temperature air. At Step 506, the water cellular enzyme is removed and/or inactivated. At Step 508, the leaves are pulverized. At Step 510, solvent is added to extract the polyphenols.

Figure 6:
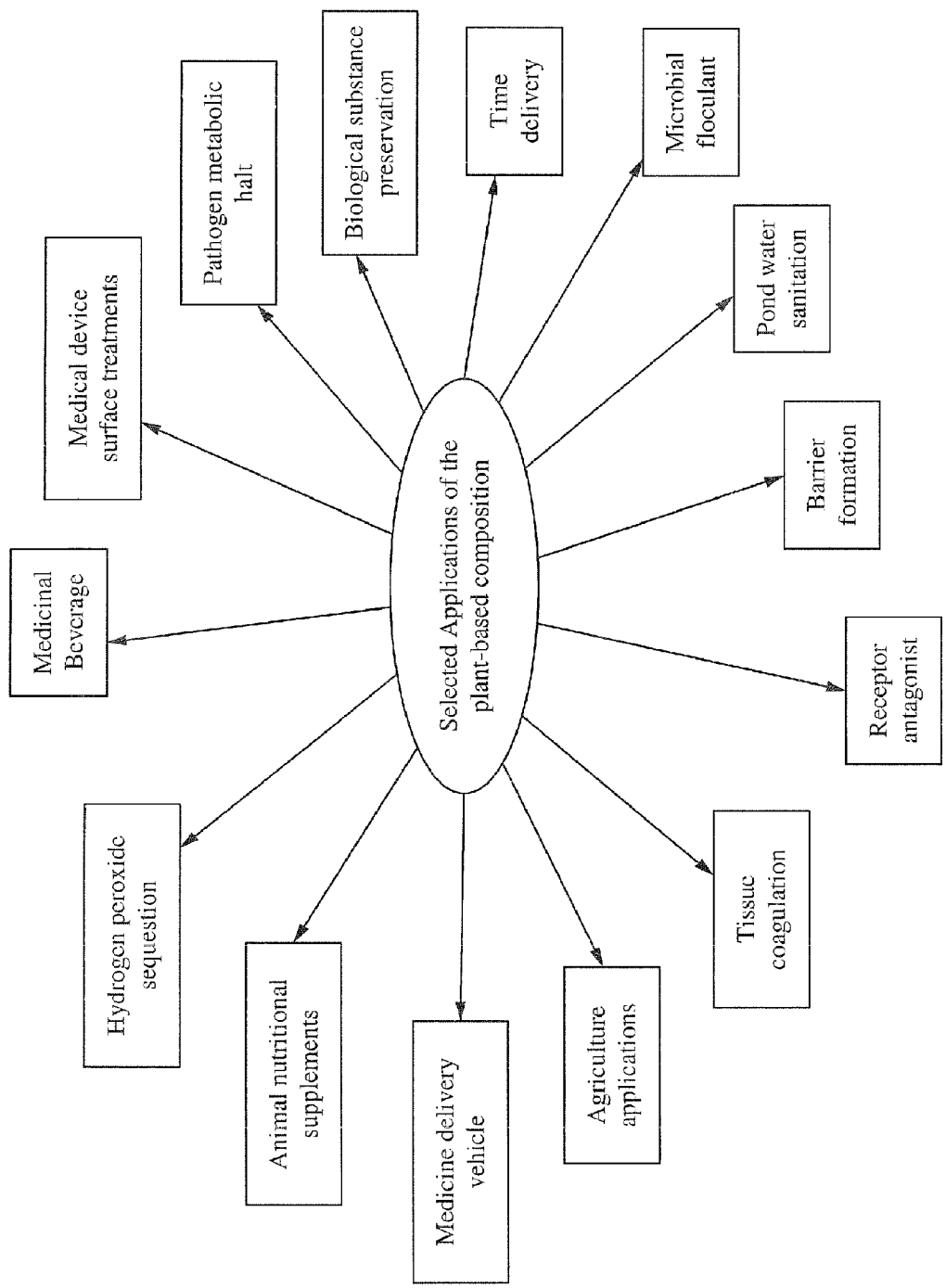
FIG. 6 illustrates applications of the plant-based composition in accordance with some embodiments.

FIG. 6 illustrates some applications of the plant-based composition in accordance with some embodiments. The applications include animal nutritional supplements, animal tissue coagulation, pathogen barrier formation, target triggering reactions, exogenous addition of oxidative enzyme for biocidal applications, hydrogen peroxide sequestration, timed delivery, pathogen metabolic halt, medicinal beverages, receptor antagonists, microbial flocculants, biological substance preservation, antimicrobial wash, agriculture applications, pond water sanitation, medical device surface treatments, and medicine delivery vehicles, to name only a few such applications.

Some modes of action in accordance with embodiments include the function of target activation of a dense population of high-affinity, low-specificity binding sites on a relatively large bio-molecule substrate. In some embodiments, a whole plant extract is used. In some embodiments, a mixture of plants is blended with different dominant phenolic species and molecular weights with slightly different protein affinities, so the broadest possible range of activity can be facilitated.

Typically, the concept of drug design of conventional drugs has been focused on highly specific molecular interactions. In comparison, some embodiments of the invention use non-selective activity that is made highly effective and safe by site-specific activation. In some embodiments of the present invention, the molecular complexes traverse the digestive system in a waterborne solution of molecules that keep the necessary multiple reactive components sequestered in direct reactive proximity of each other despite diffusion gradients in high levels of dilution. This maintains full bio-availability until it encounters damaged mucosal tissues or pathogens that present appropriate enzymes to activate the complex. Activation at the site catalyzes a highly localized transformation of the passive molecular complex into an aggressive protein binder with hundreds or thousands of potential active sites, which are far more aggressive than the two binding sites found on antibodies. This highly site specific activation and non-absorbed nature of the large "sticky" polymer creates a powerful, precisely targeted action that presents minimal adverse systemic potential. An accumulation of these "sticky" plant biopolymers becomes firmly anchored to the target site and starts to mimic the highly efficient mechanical immune reaction that would normally occur at the site of a plant injury.

In some embodiments, the mechanisms in plant immunology described above are applied to animals. The mechanisms include (1) non-specific binding to functional pathways of infecting bacteria or yeasts, which can kill the bacteria or yeasts by impairing their metabolism and reproduction, (2) binding to toxins (generally proteinaceous) present at the site and/or blocking pathogens from expression of more enzymatic virulence factors, (3) immobilizing and/or impairing their motility or causing agglomeration that prevents propagation and shedding, (4) cross-linking effects of proteins of damaged cells into a physical barrier that reduces exposure to further infection or irritation, (5) binding to inflammatory signal receptors functioning as antagonists for a variety of physiologic responses, (6) disabling the cell penetration mechanism or entrapping viruses and/or preventing propagation and shedding, and (7) localized astringent and barrier effect to reduce interstitial fluid loss from damaged tissues.

In some embodiments, the effective dosages are extremely small compared to physical astringents used in the traditional method to arrest diarrhea and believed to be insufficient to create any physical astringent effect that has been associated with intestinal damage or nutritional uptake impairment associated with the use of tannins.

Some experiments are performed using the complex prepared in accordance with the embodiments of the present invention. The effectiveness of the complexes is supported by consistent observation of improved growth in pigs treated with the complexes made in accordance with some of the embodiments. The insensitivity of the complexes to dilution, the passive nature on healthy mucosa, and the minimal activity on non-pathogenic bacteria are some of the factors that enable and make low concentration waterborne delivery preferable and more effective.

The mixture prepared in accordance with some embodiments of the present invention can be useful on a tissue lesion or an irritated mucus membrane of the digestive tract, respiratory tract, urinary tract, reproductive tract or other mucosal interface within higher animals. These tissues and infecting bacteria can be a source of oxidative enzymes that catalyze the conversion of the polyphenol substrate into its oxidized form. In some embodiments, the ingestion of the phenolic/oxidizer composition described above can direct and/or indirectly convert the polyphenols into a polyquinonic (or o-polyphenol) compound through direct enzymatic conversion or auto-oxidation of hydroxyl units with an enzyme decomposed hydrogen peroxide. The polyquinonic molecule can then covalently bind to proteins of the damaged tissue cells or the surface proteins of pathogens to immobilize, inactivate, and/or condense them. The bound proteins can form a protective matrix, which reduces the ability of pathogens to colonize, provides a strong astringent effect that contracts the wound and reduces the fluid exudate. The underlying reactions can take different pathways, depending on the specific enzymes, the structure and type of the polyphenol molecule, the relative concentration of the oxidizer, the dilution environment, etc. An oxidizer that is not directly involved in enzymatic formation of quinonic units can release oxidative radicals that directly damage cellular structures of the pathogens. The localized burst of such radicals in proximity of immobilized pathogens creates a focused germicidal action that is far more efficient than the diffuse action of germicides in free solution. The use of more than one plant material as substrates or combinations with plants with known germicidal activity without oxidation as additional constituents can be desirable for increasing the spectrum or potency of antimicrobial activity.

In other embodiments, the oxidative enzymes can be delivered to the reaction site separately. As an example, one of the embodiments contains fighting viruses in the absence of infected tissue or bacteria by providing a source of catalyzing enzymes. Viral envelopes generally do not have the enzymes, but are made up of proteins that can be bound by the macromolecule once converted into a polyquinone. The use of such a pre-converted polyquinone is applicable in some embodiments.

Some embodiments of the present invention can be used in solution as a germicidal additive. It can be triggered by the enzymes of microorganisms, such as bacteria and fungi, in the absence of other plant or animal tissue. The germicidal effectiveness on surfaces or in solution can be further enhanced by the addition of an enzyme or other catalyst to the surface or solution to be treated or by the application of the compositions to a surface, implement, or vessel that is treated with an activating enzyme or catalyst.

Some embodiments of the present invention can be used as a microbial floculant, aggregating the microorganisms into masses that either precipitate or can be filtered out by mechanical means. The aggregation of germs and their products can also increase the potential antigenicity to evoke immune responses. Astringent activity can be cytotoxic to the germs as the result of (1) cross linking that disables the germ cells' surface proteins and enzymes or receptors, signal transduction components, nutritional absorption and transfer functions and (2) reducing or impairing the mobility of germs and viruses. Both types of actions can disable the infectivity of viruses.

The bactericidal test demonstrated that an amount of hydrogen peroxide that can be exhausted by the bacteria in 16 hours can be used to completely kill all bacteria, without being consumed, when a composition made in accordance with the embodiments of the present invention is used. The plant-based material that did not undergo oxidization reactions did not show any bactericide effect. This indicated that at least some of the soluble polyphenolic compound was converted to polyquinone. In an in-vivo environment, this plant based germicidal effect will be further increased if the amount of catalase or peroxidase is not so limited. A transformed tobacco plant with a chimeric tobacco anionic peroxidase is capable of producing a high level peroxidase, demonstrated to be 7 times faster at wound healing than a non-transferred tobacco plant. The increased efficiency of the polyphenol to quinone conversion is more likely due to the significant amount of enzymes than to the amount of the substrate.

Some aspects of the present invention include the protein cross linking capability. Tannin has well known protein binding ability. However, tannin-protein binding is hydrogen bond based and the preferred binding protein is proline-rich-protein, usually in the saliva, and mucus fluid of digestive system. The protein cross linking and precipitation test demonstrates that the egg albumin formed dense and complete precipitation within 10 minutes. The precipitation with plants only takes 3 days to receive similar results. The sample with the oxidizing agent only had no precipitation effect at all. This indicates the embodiments of the present invention have greatly increased protein cross linking capacity and efficiency.

Some of the embodiments include a mixture of a plant based germicidal and a protein cross linker composition and oxidizer. The plant based germicidal and protein cross linker composition can contain a plant having high phenolic compounds. The oxidizer can be hydrogen peroxide. Some of the methods that can be used to manufacture such compositions are disclosed in the U.S. patent application Ser. No. 12/317,638, filed Dec. 23, 2008, and entitled "PLANT-BASED BIOCIDAL MATERIALS AND SYSTEMS," which is hereby incorporated by reference in its entirety.

Some embodiments of the present invention can be applied to the oxidation-reduction and/or radical reactions of the plant phenolic compounds. The plant phenolic compounds can include phenols, polyphenols, hydroxycoumarins, flavonoids, alkaloids, and any other components with chemical subunits similar to monophenols or diphenols to oxidize, to reduce, or to crosslink other molecules in or on microorganisms, plants, and animals, thereby, generating antimicrobial effects, antiviral effects, astringent effects, and wound healing effects on different target organisms or tissues. The terms "quinone" and "polyquinone" used in the present disclosure include any monomer or organic polymer of aromatic ring configurations with one or more double bonded oxygen.

The compositions and methods can be utilized to facilitate the healing of the damaged wound on the skin or apply to the digestive system for healing of any infection of the digestive system. The compositions and methods can also be utilized in various targeted environmental applications, such as in-vitro and in-vivo uses.

In some embodiments, the applications of the present invention include antimicrobials, anthelmintics, anti-laxatives/anti-diarrheas, analgesics, anti-inflammatories, cosmetic ingredients, keratolytics, oxidizers for industrial processes, metal chelating agents, and organic adhesives. In alternative embodiments, the physiologic uses include antiseptics, disinfectants, virucides, fungicides, astringents, tissue adhesives, wound protectants, biofilm preventions, anti-inflammatories, analgesics, haemostasis, product preservatives, coagulants, flocculants, oral rinses, irrigants, debriding agents, gastric tonics, anti-diarrheal, ulcer treatments, sclerotizing agents, water sanitizers, water preservatives, oxidizing cleaners, and deodorizers. In alternative embodiments, the applications include having the humans or animals ingest the compositions to treat or prevent pathogens or pathogenic molecules from infecting, damaging, or being absorbed by the tissues of their digestive systems. In other embodiments, the applications include the prevention or treatment of animal diarrhea through the reduction of fluid secretions through astringent, anti-inflammatory, or anti-microbial action. In some embodiments, the applications include the treatments of gastric reflux erosions, peptic ulcers, or other lesions of digestive system. In alternative embodiments, the applications include the treatments of nasal or aural cavity irritations or infections. In other embodiments, the applications include antimicrobial sprays to the respiratory tract to reduce the pathogens and also to protect the respiratory tract lining from invasion by the pathogens, such as bacteria, viruses, and fungi. In some embodiments, the applications include respiratory tract sprays and sinus rinses to flush the contact allergens. In alternative embodiments, the applications include urinary tract rinses for anti-infective or anti-inflammatory treatments or routine antiseptic rinses for urinary tract implant and kidney dialysis patients. In other embodiments, the applications include antiseptic organ preservation for organ transplantation.

In some embodiments, the applications include an antimicrobial wash for bacteria, viruses, and yeast infections on normal or damaged skin, surface wounds, or in any mucosal cavity. In alternative embodiments, the applications include tissue adhesives for accelerated healing, closure, or haemostasis of surgical incisions or injuries. In other embodiments, the applications include treatments of surgical incisions or topical wounds for scar reduction. In some embodiments, the applications include first aid treatment for topical cuts, burns, or abrasions. In alternative embodiments, the applications include antiseptic salves, ointment rinses, or irrigants for oral mucosal ulcer treatment, and dental procedures. In other embodiments, the applications include periodontitis treatments and sensitive-tooth treatments, such as tooth microcrack sealing. In some embodiments, the applications include oral rinses for halitosis. In alternative embodiments, the applications include soaks for dermatitis, jock itch, vaginal infections, and athlete's foot. In other embodiments, the applications include burn, chronic wound, and ulcer antimicrobial and healing treatments. In some embodiments, the applications include the prevention or reduction of biofilm formation on tissues or surfaces.

In alternative embodiments, the applications include agriculture applications. For example, the surface pathogen can be reduced and the micro-wounds can be sealed by spraying or soaking the plant with the polyphenol-oxidizer composition. Further, the general health of the plants can be improved by strengthening the surface structure or stimulating enhanced growth or development by the cross-linking reactions.

In other embodiments, the applications include aerosol or liquid sprays of the composition as a bio-security sanitizer for animal farm facilities. In some embodiments, the applications include animal feed sterilization. In alternative embodiments, the applications include food or water additives for preservation and prevention of disease transmission. In other embodiments, the applications include plant, fresh fruit, and vegetable washes. The spraying or rinsing a solution containing the composition disclosed herein can kill or suppress surface bacteria, extend shelf life, and protect the surface from or deter pest-invasion in live crops or agricultural produce. In some embodiments, the applications include plant seed disinfection for storage and sanitation before germination. In alternative embodiments, the applications include preservation spray or water treatment for freshly cut flowers. In other embodiments, the applications include tissue adhesive for plant grafting and groundwater remediation.

In some embodiments, the applications include meat and sea food preservation spray to reduce bacteria and to form thin anti-digestive layers to prevent a microbial invasion. The alternative embodiments include meat processing sanitizers for prevention of microbial contamination. In alternative embodiments, the applications include pond water sanitation for fisheries, such as fish, shrimp, oyster, abalone, and mussels. In other embodiments, the applications include disease treatment for aquatic plants and animals. In some embodiments, the applications include aquarium sanitizers, preservative additives for liquid-containing products, disinfectant ingredients for surface cleaners, quinone REDOX cycling coatings for medical devices, clothing and food preparation equipment, hospital environment and instrument sanitization, antimicrobial hydrating solutions for hydrophilic coated medical devices, and organic anti-corrosive treatments for metals.

In alternative embodiments, the applications include industrial water shock, preservatives, or antifoulants. In other embodiments, the applications include hot tub and swimming pool water sanitation. In some embodiments, the applications include carriers for small molecule therapeutic compounds. In alternative embodiments, the applications include stabilizers for oxidizers, modification of food flavors, and injection into tumors and cysts.

In some embodiments, the compositions are able to be in a dry powder form. The composition is able to be fed to an animal in a dry powder form or in a combination with at least one fluid. The compositions in a dried form are able to contain polyphenol or polymeric molecules, reactive oxygen species, catalysts, or a combination thereof. The reactive oxygen species can contain sodium percarbonate, potassium percarbonate and/or any other substance that is capable of activating the polyphenol and/or the polymeric molecules. The reactive oxygen species, the material containing polyphenol or polymeric molecules, a catalyst, or a combination thereof are able to be fed to animals concurrently or separately.

In some embodiments, the term "polyphenols" used herein contains more than one phenol unit or building block per molecule. In alternative embodiments, the term "polyphenols" contains one phenol unit per molecule. In other embodiments, the term "polyphenols" includes hydrolysable tannins (Gallic acid esters of glucose and other sugars) and phenylpropanoids, such as lignins, flavonoids, and condensed tannins.

In some embodiments, the hydrogen peroxide added to a polyphenol contained solution is 1~2%. In alternative embodiments, the hydrogen peroxide added to a polyphenol contained solution is less than 10%. A person who has ordinary skill in the art would appreciate that any concentrations of hydrogen peroxide are applicable so long as the concentration of the hydrogen peroxide is not too high to overreact with the polyphenols in the solution. The overreacting reactions include providing a concentration of hydrogen peroxide, which makes the activated polyphenols unable to perform the functions described in the present application.

In some embodiments, the term "fluid" used herein includes liquid, gas, supercritical fluid, a mobile solid form of substance, or a combination thereof. In some embodiments, the term "pathogen" includes any infectious agents, gems, bacteria, virus, or a combination thereof. In some embodiments, the term "pathogen" includes any biological substances that can potentially cause disease, illness, damage, harm, or negative impact to a host, such as an animal or another biological substance. In some embodiments, the term "biopolymer" includes any substances that can be derived or obtained from a plant, an animal, or biological substances. In alternative embodiments, the term "biopolymer" includes any polymeric molecules produced by a biological organism, such as a live plant. Further, the term "biopolymer" can include cellulose and starch, proteins and peptides, and DNA and RNA. In some embodiments, the term "biopolymer" includes plural units of sugars, amino acids, and nucleotides. In some embodiments, the teen "binding affinity" includes any intermolecular or intramolecular interactions and/or bondings. For example, covalent bonds, ionic bonds, hydrogen bonds, dipole moments, induced dipole moments, and electrostatic forces. In some embodiments, the term "reactive proximity" refers to any interaction that exists between two or more molecules/atoms, so that the two or more molecules are not randomly freely moving in a solution.

In some embodiments, the term "effect in inactivating a pathogen" disclosed herein includes blocking pathogens from accessing animal/plant tissues, smothering the metabolic pathways of the pathogens, binding viral factors, immobilizing/aggregating the pathogens, and/or performing oxidative damages to the pathogens. In some embodiments, the sources of reactive oxygen species and/or hydrogen peroxide are able to be obtained from natural and artificial sources, such as a flesh aloe and/or cilantro. In some embodiments, the activated polyphenol include o-polyphenol, oxidized polyphenol, polyphenone, and polyquinone.

The term "process fluid" is able to include a fluid that is artificially and/or biologically processed. The term "biologically processed" is able to refer that an added composition is processed by a biological substance, such as an animal. The term "artificially processed" is able to include filtration, desiccation, isolation, extraction, or any other manufacturing or chemical/biological lab processes. For example, the term "process fluid" is able to include the situation that a dry powder form of substances is fed to animals and having a fluid of the animals or added fluid to dissolve or disperse the dry powder, thereby forming a processed fluid. The dry powder is able to contain both polyphenols and reactive oxygen species, such as sodium percarbonate and potassium percarbonate, to be fed to the animals. Alternatively, the dry powder is able to contain mainly polyphenols. The reactive oxygen species is able to be fed to the animal in a liquid form together or separately with the dry powder. In another alternative embodiment, the dry powder form is able to contain mainly reactive oxygen species. The polyphenols or hydroxyl groups contained molecules are able to be fed to the animals in a liquid form together or separately with the dry powder.

The following experiments show the effectiveness of the compositions prepared in accordance with some of the embodiments of the present invention.

EXPERIMENT 1

Three samples of purified powdered bovine serum albumin (BSA) were prepared in aqueous solution. Sample #1 contained BSA only. Sample #2 contained BSA and polyphenol oxidase. Sample #3 contained BSA, polyphenol oxidase, and hydrogen peroxide. Each sample showed similar steady state turbidity after 30 minutes as measured by a spectrophotometer. An aqueous solution of polyphenols (tannin) from Chinese Gall was added to each of the samples. After one hour, Sample #1 showed little visible change. Sample #2 exhibited an increase in turbidity from increased particle size, indicating minor protein coagulation. Sample #3 exhibited heavy precipitate on the bottom of the test tube and a lack of turbidity, demonstrating that a substantial increase in protein coagulation can be achieved by the enzymatic reaction of polyphenols with a source of reactive oxygen species.

EXPERIMENT 2

A solution of Chinese Gall and hydrogen peroxide was added to (1) a tube containing powdered chicken egg white (the desiccation processes used in manufacturing powdered egg white denatures enzymes) reconstituted in water and (2) a tube containing fresh chicken egg albumin in water. Much greater precipitation was observed in the fresh chicken egg albumin sample, demonstrating that plant polyphenols can be catalyzed by enzymes of animal origin to increase protein binding consistent with quinone formation exhibited in plant wounding.

EXPERIMENT 3

Formulation A was prepared using the method described below. One gram of commercial green tea powder was prepared in 1 liter of deionized water in a 1 liter Pyrex beaker and allowed to extract at room temperature for 6 hours. 35% food grade hydrogen peroxide was added to the solution and allowed to sit for 4 hours, then filtered through a 2 micron mesh media or filter. The resulting stock solution was diluted 1000:1, 200:1, and 100:1 with 18 Mohm water. 15 ml of dilute solutions was added to equal part culture solutions containing 10 e7 wild strain *E. coli* cultures (water controls) and allowed to incubate at 37° C. At 2 hr, 4 hr, 6 hr, and 8 hrs, a sample from each test series was flooded on agar plates and incubated, and manual colony counts were performed. The 100:1 sample achieved 100% kill at 4 hrs, the 200:1 achieved 100% kill at 6 hrs, and the 1000:1 was only bacteriostatic. This demonstrates the feasibility of manufacturing a botanical based composition with high germicidal capabilities with exceptionally low raw material and energy input.

EXPERIMENT 4

A wild strain *E-Coli* culture was added to three samples. The sample A contained 25 ppm hydrogen peroxide in water. The sample B contained a solution of Formulation A diluted to equivalent 25 ppm hydrogen peroxide fraction. The sample C contained a solution having a green tea extract of the same concentration of Formulation A but without hydrogen peroxide. The bacteria's population in the hydrogen peroxide (the sample A) was initially reduced but began to exhibit increased visual turbidity after 16 hours, indicating the exhaustion of antimicrobial capability. The green tea extract alone (the sample C) exhibited little noticeable antimicrobial activity. Formulation A (the sample B) continued to kill the bacteria and showed no rebound after 3 days, indicating 100% kill and/or increased antimicrobial effectiveness, which demonstrates significantly enhanced germicidal performance resulting from the combination of green tea extract and hydrogen peroxide.

EXPERIMENT 5

Sample #2 was a pre-prepared solution using the Formulation A above, which was diluted to duplicate the same polyphenol concentration as a pre-prepared Sample #1. In Sample #3, polyphenol and dilute hydrogen peroxide were combined to achieve the same ratio of polyphenol to hydrogen peroxide as in Sample #2. Serial dilutions of each sample were prepared and left standing for 24 hours. A solution containing 10e5/ml wild strain *E Coli* was added to each sample, which was then incubated and plated out on agar for visual colony counts. The pre-prepared polyphenol-oxidizer solutions of Sample #2 continued to kill bacteria effectively at significantly lower concentrations than in the Sample #3 dilutions, demonstrating the enhanced performance at low concentrations when a polyphenol substrate-oxidizer composition is produced at a high concentration (in the absence of active oxidoreductases or other reducing agents) before dilution, supporting the concept of intermolecular force sequestration for improved stability.

EXPERIMENT 6

The following is a method of preparing Formulation B and a demonstration of a polyphenol substrate extraction process. 30 grams of dried pomegranate rind is used, which was dried at 150 C for 1 hr, grounded to fine powder, and combined with 10 liters of deionized water heated to 80 C for 20 minutes, then was cooled to room temperature for 2 hours. 35% food grade hydrogen peroxide was added and allowed to sit for 6 hrs, and then filtered through a 5 micron media. The added hydrogen peroxide solution was less than 10% in solution after added into the solution to prevent overreacting with the polyphenols. Serial water dilutions of the resultant solution were added to 10e7-10e8 liquid bacteria cultures. The resultant solution was incubated for 24 hrs and visually observed for turbidity. As shown in Table 1, the turbidity (+turbid, −not turbid) indicates viable bacteria.

EXPERIMENT 9

Ten human volunteers with current and a history of past symptoms of frequent or chronic diarrhea were given 5 ml of 40:1 dilution of Formulation B in 250 ml of water for 5 days. Nine expressed significant reduction in discomfort and symptoms for 1 week or more.

EXPERIMENT 10

0.5 ml of 100:1 dilution of Formulation A and Formulation B were introduced into a punch well on a sheep blood infused agar plate that was surface inoculated with *e-coli*. The perimeter of the well quickly formed an opaque area of cross linked blood proteins that were refractory to penetration of the PP-O complex and showed no bacterial suppression zone around the well. In comparison, minimal nutrient agar without blood proteins showed a significant suppression zone indicative of PP-O diffusion through the medium, demonstrating the low tissue penetration of the compositions supporting reduced toxicity potential.

EXAMPLE 11

5-day-old Asian Landrace hybrid pigs in a commercial farm were divided into 13 test subjects and 3 control subjects, all fed identical quantities and types of feed from birth to 3 months. Test subjects were given 5 micrograms (dry plant weight equivalent) of Formulation A every third day in feed water and the same dose daily if diarrhea was observed. Controls were given antibiotic injections to treat diarrhea. At 21 days, the test group encountered less diarrhea and an average were 1.0 kg heavier than the controls. At 3 months the average weight of the test subjects was between 25-30%

TABLE 1

| Bacterium species | Concentration (ug/ml) | | | | | | | | | | | |
|---|---|---|---|---|---|---|---|---|---|---|---|---|
|  | 500 | 250 | 125 | 62.5 | 31.3 | 15.6 | 7.81 | 3.9 | 1.95 | 0.98 | 0.49 | Control |
| *Escherichia coil* | − | − | − | − | − | − | − | − | + | + | + | + |
| *Salmonella enterica St. Typh.* | − | − | − | − | − | − | − | + | + | + | + | + |
| *Staphylococcus aureus* | − | − | − | − | − | − | − | − | + | + | + | + |
| *Pseudomonas aeruginosa* | − | − | − | − | − | − | − | + | + | + | + | + |
| *Listeria monocytogenes* | − | − | − | − | − | − | + | + | + | + | + | + |
| *Pasteurella multocida* | − | − | − | − | − | − | − | + | + | + | + | + |
| *Proteus vulgaris* | − | − | − | − | − | + | + | + | + | + | + | + |
| *Klebsiella pneumoniae* | − | − | − | − | − | − | − | − | + | + | + | + |
| *Bacillus cereus* | − | − | − | − | − | − | − | − | + | + | + | + |
| *Bordetella brochiseptica* | − | − | − | − | − | − | − | − | + | + | + | + |

EXPERIMENT 7

The application of a 200:1 dilution of formulation A to bilateral symmetric lancet wounds on laboratory mice demonstrated wound closure in approximately one third of the wounds treated with a saline control or antibiotic ointment.

EXPERIMENT 8

A cotton pad soaked in a 200:1 dilution of Formulation A was applied to inflamed oral mucosa for 10 minutes. Of three volunteers, all experienced significant reduction in pain and swelling within one hour. Infection was completely resolved in two, demonstrating anti-inflammatory and anti-infective potential on mucosal tissue.

greater than that of the controls based on girth measure, demonstrating Formulation A's viability as an alternative to antibiotics as a prophylactic and growth promoter.

EXPERIMENT 12

The growth of 99 purebred Landrace piglets was tracked and evaluated. The piglets were fed an oxidizer-polyphenol composition of Formulation B in Swine milk replacer. 21-day-old starters tend to be stressed by environmental transition and have increased incidences of diarrhea for approximately one week. The experimental group showed 18% higher average weight gain during this period than the control group, demonstrating commercial value in growth optimization and compatibility with milk replacer.

TABLE 2

|  | Experimental Group | Control Group |
| --- | --- | --- |
| No. of Piglets | 53 | 46 |
| Dosage | 7.5 µg (dry plant wt) | 0 µg |
| Frequency | Once per day | None |
| Testing period | 8 days | 8 days |
| Avg. wt. at beginning | 7.00 kg | 7.225 kg |
| Avg. Wt. at the end | 8.81 kg | 8.76 kg |
| Average weight gain | 1.81 kg | 1.535 kg |

EXPERIMENT 13

Toxicological safety was tested using 10 specific pathogen-free purebred landrace pigs, each 23 days old. The pigs were administered one 250 µg or one 2500 µg dose daily for 45 days. Hematology and growth were monitored and histology performed, showing no negative effect on tissue or organs.

EXPERIMENT 14

50 weaned starter piglets were divided into 5 groups and each given 12 µg dose once every third day for 5 weeks. Statistical analysis shows superior weight gain in experimental groups. The above experiments are evidence of the effective uses of polyphenol-oxidizer compositions in the control of pathogens and show measurable value in numerous commercial and medically useful applications. Although the experiments demonstrate direct growth promotion benefits in agricultural animal production, the use of swine are known to have close physiologic and immunologic similarities to humans and are commonly used as predictors of performance and safety in humans. Potential effects can therefore be projected and claimed for humans. This is supported by direct experience in the rapid quelling of occasional digestive discomfort and diarrhea of non-specific causes. Single doses ranging from 20 µg to 250 µg (dry wt. equiv.) have been observed to be effective in resolving diarrhea in humans, with symptomatic relief typically noticed within one hour.

Production

Some of the embodiments have been produced according to the methods described herein. The manufacturing process can use organic production materials and procedures using National Organic Program (NOP) approved and Generally recognized as Safe (GRAS) food-grade materials. The manufacturing process can be carried out in a clean-room laboratory under Good Manufacturing Practice (GMP).

Some methods of production include botanical pre-process, protein denaturization and extraction, intramolecular sequestration of reactants into meta-stable phenolic complex, post processing, and dilution and formulation with additional ingredients.

The process disclosed herein is applicable to a wide range of plant species and tissue types due to the ubiquitous nature of the chemistry of interest. The sources of the plant can be chosen based on the availability of cultivation sources, key fraction content and secondary constituents that can potentially impart desirable or undesirable characteristic effects, such as toxicity and auto-degradation.

The manufacturing of the composition disclosed herein can incorporate several standardized quality control methods that directly measure substrate contents, initiator potency, microbiologic performance, and molecular binding capacity. The manufacturing of the composition had been tested in room temperature for over a year. The result shows accelerated stability testing with retained samples. The microbiologic stability dilution threshold of the compound has been determined to be above that which makes it is self-preserving.

Some of the embodiments have been successfully produced from a variety different plant bases. Preferred results are obtained when non-controversial well characterized food plants with a long history of use in complementary and alternative medicines are used. A person of ordinary skill in the art would appreciate that many plants, plant tissues or combinations can be used to make different formulations for different markets, as long as the working mechanism is functionally, structurally, chemically, biologically, or physically equivalent to the embodiments described herein.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that various modifications may be made to the embodiments chosen for illustration without departing from the spirit and scope of the invention as defined by the appended claims.

We claim:

1. A multi-component, antibacterial composition consisting of a product prepared by a process having the steps of
  (i) combining *Camellia sinensis* with water to create a first formulation, the creating including heating at 80° C. to 150° C. to substantially denature enzymes endogenous to the *Camellia sinensis*;
  (ii) combining pomegranate rind with water to create a second formulation, the creating including heating at 80° C. to 150° C. to substantially denature enzymes endogenous to the pomegranate rind;
  (iii) adding from 1% to less than 10% of hydrogen peroxide to the first formulation and the second formulation after the combining and heating, and,
  (iv) combining the first formulation with the second formulation.

2. A dry form of the antibacterial composition of claim 1.

3. The antibacterial composition of claim 1, wherein the composition endogenously contains a component selected from the group consisting of a tannin, a lignin, a flavonoid, a hydroxycoumarin and an alkaloid.

4. The antibacterial composition of claim 1, wherein the composition is in a dose ranging from 20 µg to 250 µg.

5. The antibacterial composition of claim 1, wherein the heating is carried out from 80° C. to 110° C.

6. The antibacterial composition of claim 1, wherein the adding includes adding 1% to 2% of hydrogen peroxide.

7. A method for treating a bacterial infection, comprising administering to a subject in need thereof, an effective amount of the antibacterial composition of claim 1.

8. A method of treating bacteria-infected water, comprising administering to the water an effective amount of the antibacterial composition of claim 1.

9. A method of treating or preventing a bacterial infection in a wounded tissue, comprising administering to the tissue, an effective amount of the antibacterial composition of claim 1.

10. A method for treating a bacterial-infected tissue, comprising administering to the tissue, an effective amount of the composition of claim 1.

* * * * *